US012577250B2

(12) United States Patent
Xie et al.

(10) Patent No.: US 12,577,250 B2
(45) Date of Patent: Mar. 17, 2026

(54) 1,2,4-TRIAZOLONE DERIVATIVE AS DHODH INHIBITOR, AND PREPARATION METHOD THEREFOR AND USE THEREOF

(71) Applicant: WIGEN BIOMEDICINE TECHNOLOGY (SHANGHAI) CO., LTD., Shanghai (CN)

(72) Inventors: Yuli Xie, Shanghai (CN); Houxing Fan, Shanghai (CN); Lihui Qian, Shanghai (CN)

(73) Assignee: WIGEN BIOMEDICINE TECHNOLOGY (SHANGHAI) CO., LTD., Shanghai (CN)

( * ) Notice: Subject to any disclaimer, the term of this patent is extended or adjusted under 35 U.S.C. 154(b) by 354 days.

(21) Appl. No.: 18/288,803

(22) PCT Filed: Jul. 5, 2022

(86) PCT No.: PCT/CN2022/104004

§ 371 (c)(1),
(2) Date: Oct. 27, 2023

(87) PCT Pub. No.: WO2023/280181

PCT Pub. Date: Jan. 12, 2023

(65) Prior Publication Data

US 2024/0287075 A1 Aug. 29, 2024

(30) Foreign Application Priority Data

Jul. 5, 2021 (CN) ........................ 202110757483.X

(51) Int. Cl.

| | |
|---|---|
| ***C07D 487/04*** | (2006.01) |
| ***A61K 31/4196*** | (2006.01) |
| ***A61K 31/437*** | (2006.01) |
| ***A61K 31/444*** | (2006.01) |
| ***A61K 31/55*** | (2006.01) |
| ***A61P 35/00*** | (2006.01) |
| ***C07D 471/04*** | (2006.01) |

(52) U.S. Cl.

CPC ........ *C07D 487/04* (2013.01); *A61K 31/4196* (2013.01); *A61K 31/437* (2013.01); *A61K 31/444* (2013.01); *A61K 31/55* (2013.01); *A61P 35/00* (2018.01); *C07D 471/04* (2013.01)

(58) Field of Classification Search

CPC .............. A61K 31/4196; A61K 31/437; A61K 31/444; A61K 31/55; C07D 471/04; C07D 487/04; A61P 35/00

See application file for complete search history.

(56) References Cited

U.S. PATENT DOCUMENTS

2019/0375747 A1* 12/2019 Gradl ...................... A61P 35/02

FOREIGN PATENT DOCUMENTS

| | | | |
|---|---|---|---|
| CN | 110023302 | A | 7/2019 |
| CN | 110248937 | A | 9/2019 |
| WO | 2014128669 | A2 | 8/2014 |
| WO | 2020144638 | A1 | 7/2020 |
| WO | 2021038490 | A1 | 3/2021 |

* cited by examiner

*Primary Examiner* — Sarah Pihonak
*Assistant Examiner* — Padmaja S Rao
(74) *Attorney, Agent, or Firm* — SZDC Law PC

(57) ABSTRACT

The present invention relates to a 1,2,4-triazolone derivative as a DHODH inhibitor, a preparation method therefor and use thereof. Specifically, the present invention relates to a compound of general formula (1), a preparation method therefor, and use of the compound of general formula (1) and an isomer, a crystalline form, a pharmaceutically acceptable salt, a hydrate or a solvate thereof as a DHODH inhibitor in the treatment of DHODH-related diseases.

(1)

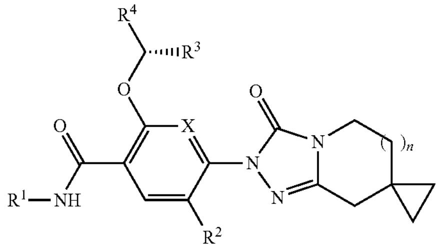

6 Claims, No Drawings

1,2,4-TRIAZOLONE DERIVATIVE AS DHODH INHIBITOR, AND PREPARATION METHOD THEREFOR AND USE THEREOF

The present application is the national stage application of PCT/CN2022/104004, filed on Jul. 5, 2022, which claims priority to Chinese Patent Application 202110757483.X filed on Jul. 5, 2021, which is incorporated herein by reference in its entirety.

TECHNICAL FIELD

The present invention relates to the field of pharmaceutical chemistry, and in particular to a novel 1,2,4-triazolone derivative, a preparation method therefor and use thereof.

BACKGROUND

Dihydroorotate dehydrogenase (DHODH) is an iron-containing flavin-dependent enzyme, which is mainly present in the inner membrane of mitochondria and is a key enzyme for de novo synthesis of pyrimidine nucleotides. The pyrimidine nucleotides are backbone components of DNA and RNA. Orotic acid is a precursor for the synthesis of the pyrimidine nucleotides. DHODH catalyzes the dehydrogenation of dihydroorotic acid to convert it into the orotic acid. Thus, inhibition of DHODH can block de novo synthesis of pyrimidine, resulting in synthesis failure of DNA and RNA.

Intracellular pyrimidine nucleotides are mainly derived from pathways of de novo synthesis and salvage synthesis. For normally differentiated resting cells, the pyrimidine nucleotides are mainly derived from a salvage pathway of direct conversion of free pyrimidine bases into the pyrimidine nucleotides, also known as a regenerative synthesis pathway. However, in the case of T and B lymphocytes which are vigorously metabolized under pathological conditions or rapidly divided cancer cells, the pyrimidine nucleotides generated by the salvage pathway cannot maintain the function or the survival of the cells. Thus, de novo synthesis of the pyrimidine nucleotides depending on DHODH is crucial for the survival of such cells. Inhibiting the activity of DHODH can selectively prevent large demand of the pyrimidine nucleotides for such cells, thereby hindering the synthesis of biomacromolecules such as DNA, RNA, and glycoproteins, and inhibiting the function or growth of the cells.

With this property, the development of DHODH inhibitors targeting aberrantly activated T and B cells as well as rapidly divided cancer cells has been shown to be successful for the purpose of treating cancers, viral infections, autoimmune diseases (rheumatoid arthritis and multiple sclerosis), etc., for example, the DHODH small molecule inhibitors leflunomide/teriflunomide and brequinar have been approved for the treatment of rheumatoid arthritis and multiple sclerosis. However, these inhibitors have high fat solubility and poor selectivity, and can generate large toxic and side effects after long-term use. Therefore, the search for novel DHODH inhibitors with high efficacy and low side effects for the treatment of immune-related diseases and tumors has become a focus of current research.

SUMMARY

The present invention provides a compound of general formula (1) or an isomer, a crystalline form, a pharmaceutically acceptable salt, a hydrate or a solvate thereof:

(1)

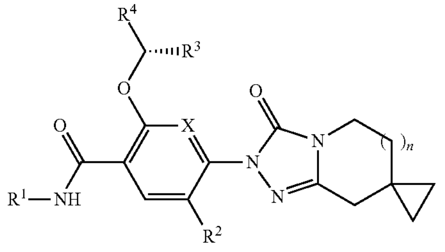

wherein in general formula (1):

n is 0, 1 or 2;

X is CH or N;

$R^1$ is aryl or heteroaryl, wherein the aryl and heteroaryl may be substituted with one or more of the following groups: halogen, $NH_2$, C1-C3 alkyl, C1-C3 alkoxy or halogenated C1-C3 alkyl;

$R^2$ is H or F;

$R^3$ is C1-C3 alkyl;

$R^4$ is C1-C6 alkyl, C3-C8 cycloalkyl or halogenated C1-C6 alkyl.

In another preferred embodiment, in general formula (1), $R^1$ is

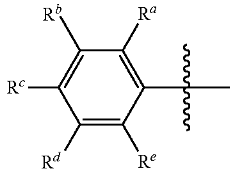,
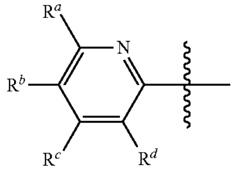,
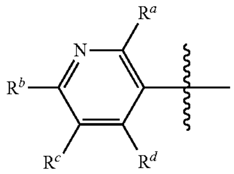,
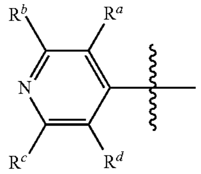 or
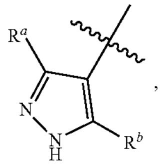, wherein $R^a$, $R^b$, $R^c$, $R^d$ and $R^e$ are independently H, F, Cl, Me, Et, OMe, $CHF_2$, $CF_3$ or $N_2$.

In another preferred embodiment, in general formula (1), $R^3$ is Me.

In another preferred embodiment, in general formula (1), $R^4$ is Me, Et, $CF_3$,

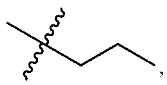,
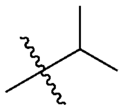,
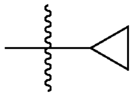,
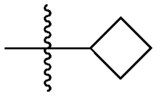,
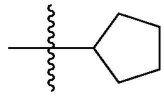 or

-continued
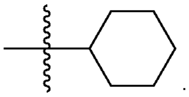
In some embodiments of the present invention, the compound or the isomer, the crystalline form, the pharmaceutically acceptable salt, the hydrate or the solvate thereof described above is selected from one of the following structures:
1
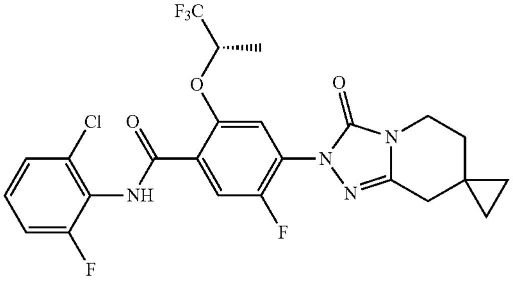
2
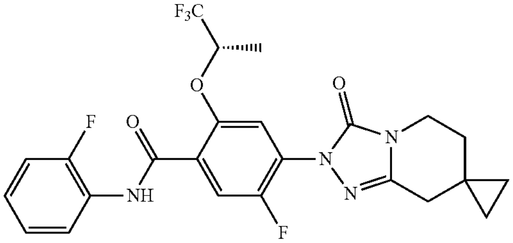 [SMILES: C[C@H](Oc1cc(-n2nc3n(c2=O)CCC2(CC2)C3)c(F)cc1C(=O)Nc1ccccc1F)C(F)(F)F]
3
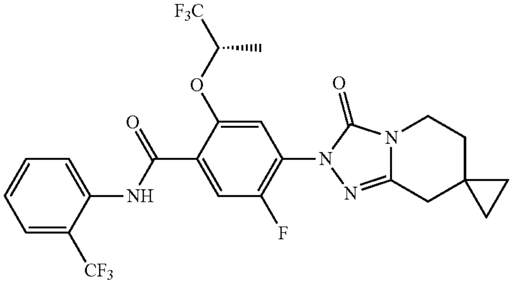 [SMILES: C[C@H](Oc1cc(-n2nc3n(c2=O)CCC2(CC2)C3)c(F)cc1C(=O)Nc1ccccc1C(F)(F)F)C(F)(F)F]
4
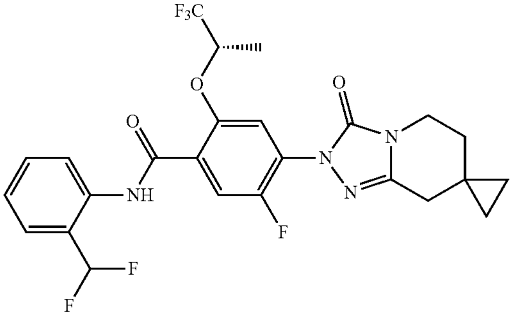 [SMILES: C[C@H](Oc1cc(-n2nc3n(c2=O)CCC2(CC2)C3)c(F)cc1C(=O)Nc1ccccc1C(F)F)C(F)(F)F]
-continued
5
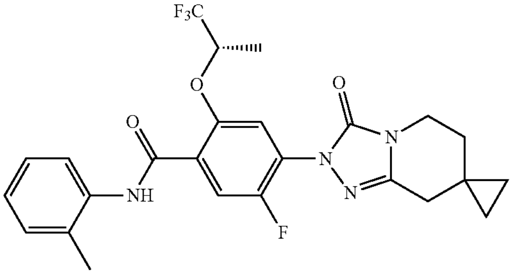 [SMILES: Cc1ccccc1NC(=O)c1cc(F)c(-n2nc3n(c2=O)CCC2(CC2)C3)cc1O[C@@H](C)C(F)(F)F]
6
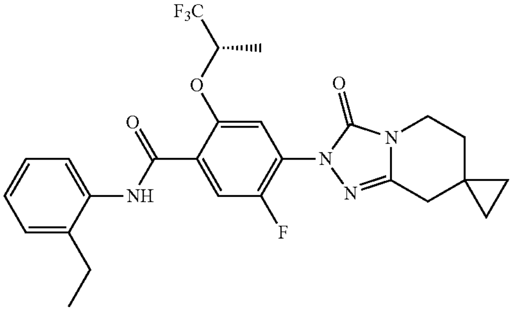 [SMILES: CCc1ccccc1NC(=O)c1cc(F)c(-n2nc3n(c2=O)CCC2(CC2)C3)cc1O[C@@H](C)C(F)(F)F]
7
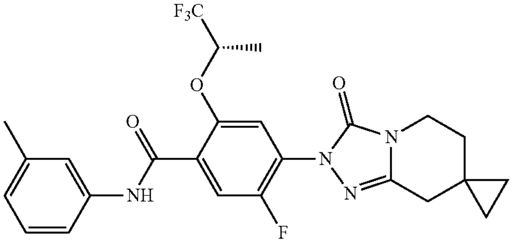 [SMILES: Cc1cccc(NC(=O)c2cc(F)c(-n3nc4n(c3=O)CCC3(CC3)C4)cc2O[C@@H](C)C(F)(F)F)c1]
8
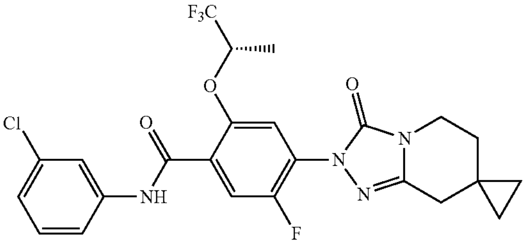 [SMILES: C[C@H](Oc1cc(-n2nc3n(c2=O)CCC2(CC2)C3)c(F)cc1C(=O)Nc1cccc(Cl)c1)C(F)(F)F]
9
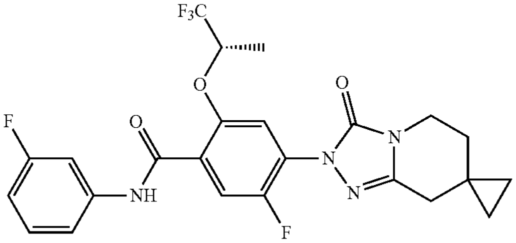 [SMILES: C[C@H](Oc1cc(-n2nc3n(c2=O)CCC2(CC2)C3)c(F)cc1C(=O)Nc1cccc(F)c1)C(F)(F)F]
10
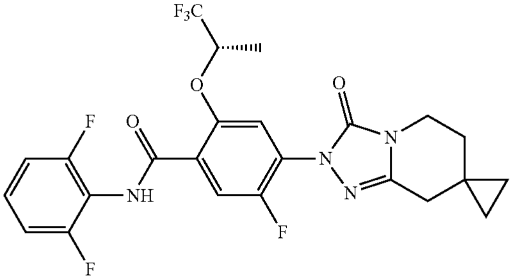 [SMILES: C[C@H](Oc1cc(-n2nc3n(c2=O)CCC2(CC2)C3)c(F)cc1C(=O)Nc1c(F)cccc1F)C(F)(F)F]

-continued
11
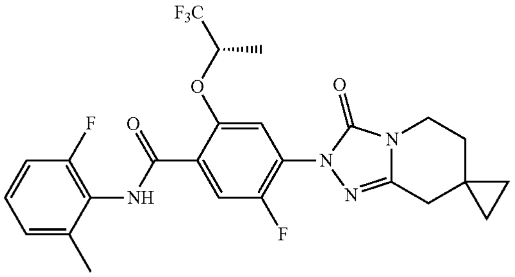
12
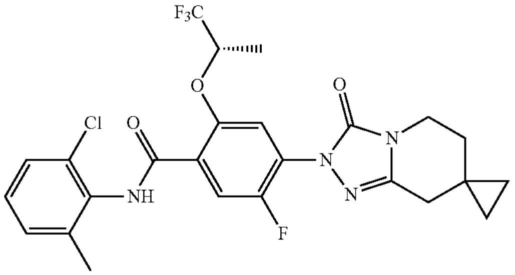
13
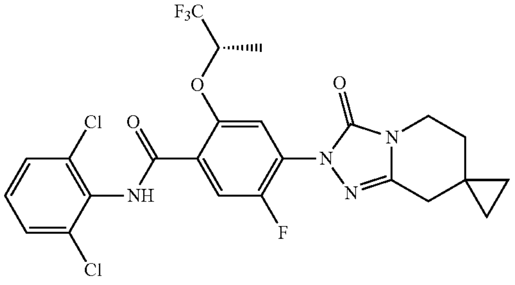 [SMILES: C[C@H](Oc1cc(-n2nc3n(c2=O)CCC2(CC2)C3)c(F)cc1C(=O)Nc1c(Cl)cccc1Cl)C(F)(F)F]
14
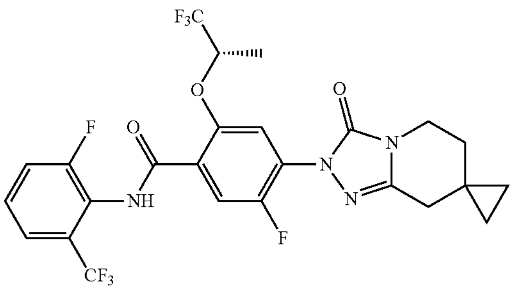
15
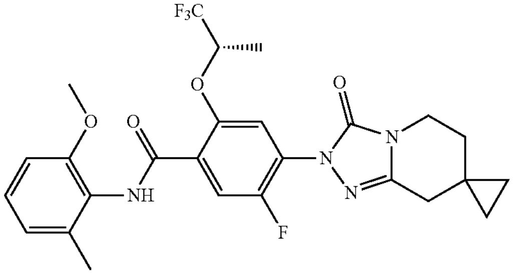 [SMILES: COc1cccc(C)c1NC(=O)c1cc(F)c(-n2nc3n(c2=O)CCC2(CC2)C3)cc1O[C@@H](C)C(F)(F)F]
-continued
16
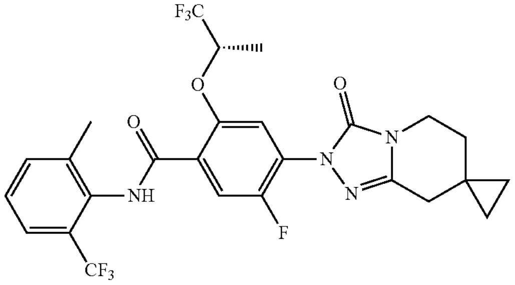 [SMILES: Cc1cccc(C(F)(F)F)c1NC(=O)c1cc(F)c(-n2nc3n(c2=O)CCC2(CC2)C3)cc1O[C@@H](C)C(F)(F)F]
17
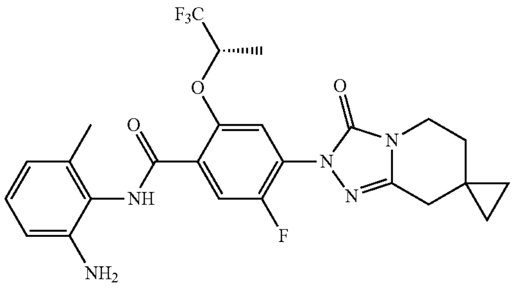
18
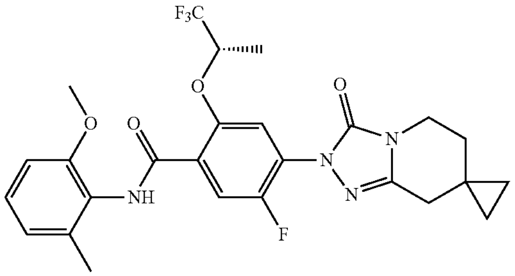 [SMILES: COc1cccc(C)c1NC(=O)c1cc(F)c(-n2nc3n(c2=O)CCC2(CC2)C3)cc1O[C@@H](C)C(F)(F)F]
19
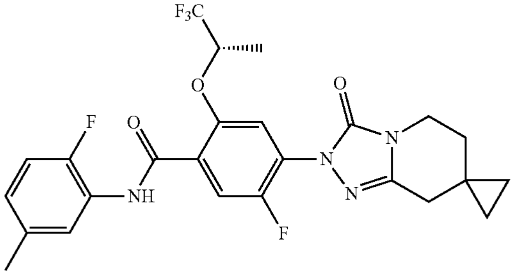 [SMILES: Cc1ccc(F)c(NC(=O)c2cc(F)c(-n3nc4n(c3=O)CCC3(CC3)C4)cc2O[C@@H](C)C(F)(F)F)c1]
20
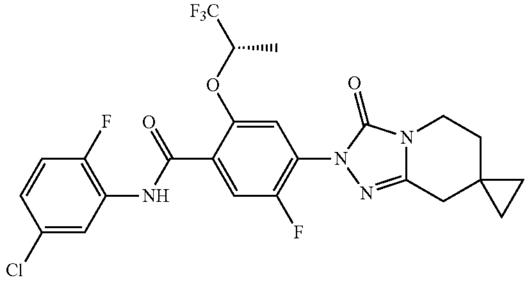 [SMILES: C[C@H](Oc1cc(-n2nc3n(c2=O)CCC2(CC2)C3)c(F)cc1C(=O)Nc1cc(Cl)ccc1F)C(F)(F)F]

-continued
21
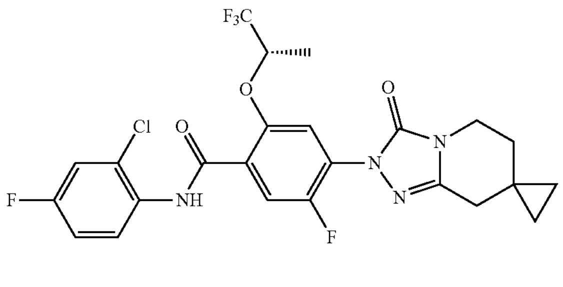 [SMILES: C[C@H](Oc1cc(-n2nc3n(c2=O)CCC2(CC2)C3)c(F)cc1C(=O)Nc1ccc(F)cc1Cl)C(F)(F)F]
22
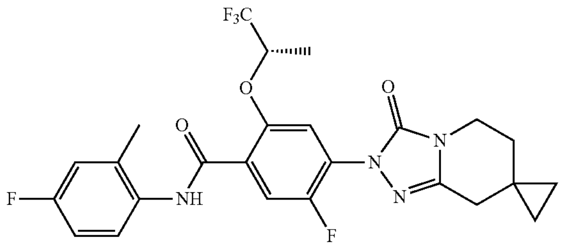 [SMILES: Cc1cc(F)ccc1NC(=O)c1cc(F)c(-n2nc3n(c2=O)CCC2(CC2)C3)cc1O[C@@H](C)C(F)(F)F]
23
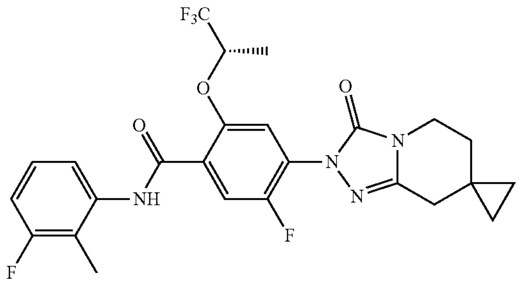 [SMILES: Cc1c(F)cccc1NC(=O)c1cc(F)c(-n2nc3n(c2=O)CCC2(CC2)C3)cc1O[C@@H](C)C(F)(F)F]
24
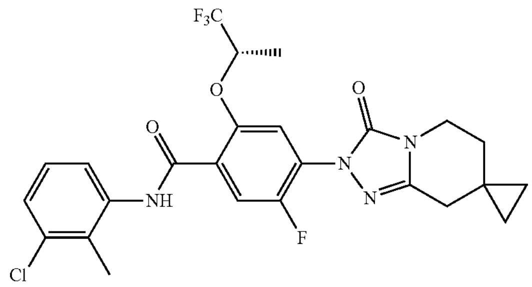 [SMILES: Cc1c(Cl)cccc1NC(=O)c1cc(F)c(-n2nc3n(c2=O)CCC2(CC2)C3)cc1O[C@@H](C)C(F)(F)F]
25
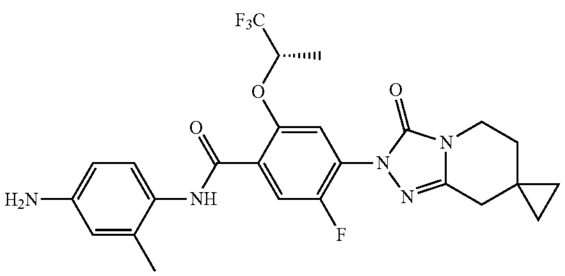 [SMILES: Cc1cc(N)ccc1NC(=O)c1cc(F)c(-n2nc3n(c2=O)CCC2(CC2)C3)cc1O[C@@H](C)C(F)(F)F]
-continued
26
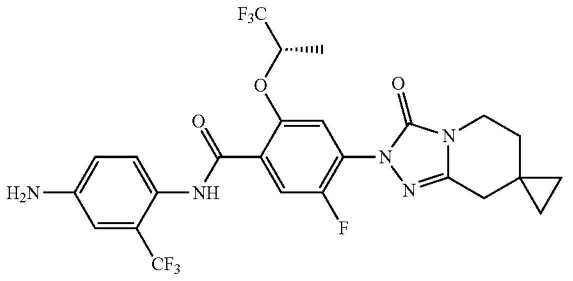 [SMILES: C[C@H](Oc1cc(-n2nc3n(c2=O)CCC2(CC2)C3)c(F)cc1C(=O)Nc1ccc(N)cc1C(F)(F)F)C(F)(F)F]
27
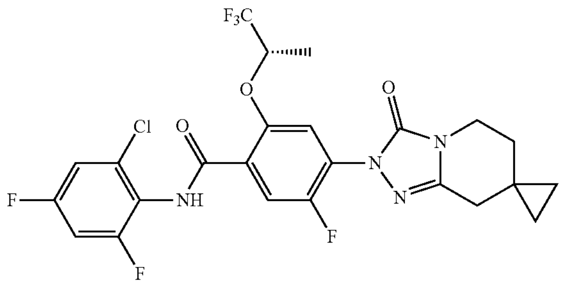 [SMILES: C[C@H](Oc1cc(-n2nc3n(c2=O)CCC2(CC2)C3)c(F)cc1C(=O)Nc1c(F)cc(F)cc1Cl)C(F)(F)F]
28
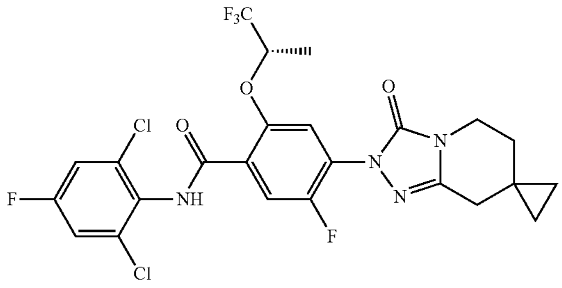 [SMILES: C[C@H](Oc1cc(-n2nc3n(c2=O)CCC2(CC2)C3)c(F)cc1C(=O)Nc1c(F)cc(F)cc1Cl)C(F)(F)F]
29
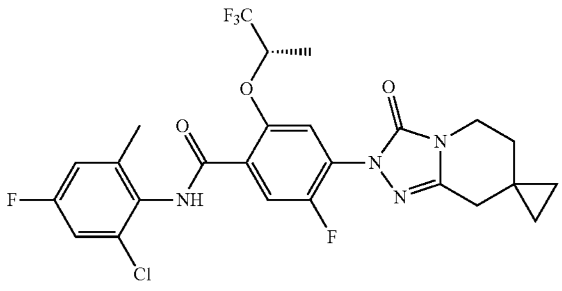 [SMILES: Cc1cc(F)cc(F)c1NC(=O)c1cc(F)c(-n2nc3n(c2=O)CCC2(CC2)C3)cc1O[C@@H](C)C(F)(F)F]
30
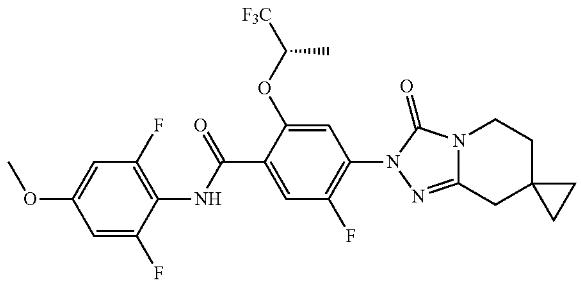 [SMILES: COc1cc(F)c(NC(=O)c2cc(F)c(-n3nc4n(c3=O)CCC3(CC3)C4)cc2O[C@@H](C)C(F)(F)F)c(F)c1]

-continued
31
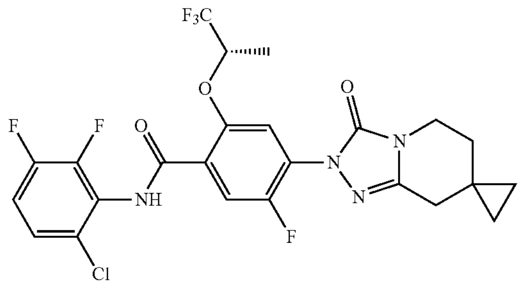 [SMILES: C[C@H](Oc1cc(-n2nc3n(c2=O)CCC2(CC2)C3)c(F)cc1C(=O)Nc1c(Cl)ccc(F)c1F)C(F)(F)F]
32
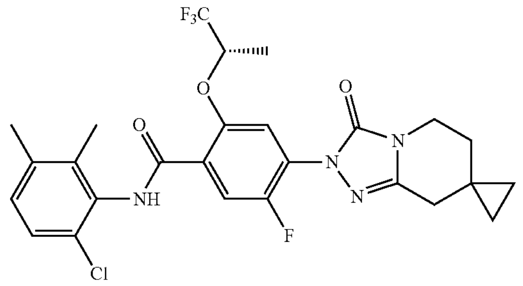 [SMILES: Cc1ccc(Cl)c(NC(=O)c2cc(F)c(-n3nc4n(c3=O)CCC3(CC3)C4)cc2O[C@@H](C)C(F)(F)F)c1C]
33
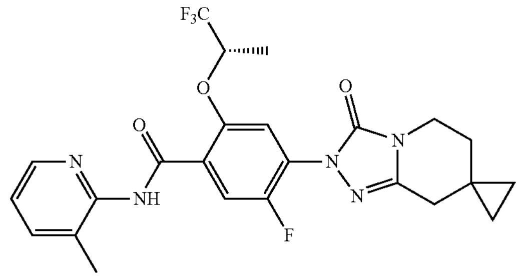 [SMILES: Cc1cccnc1NC(=O)c1cc(F)c(-n2nc3n(c2=O)CCC2(CC2)C3)cc1O[C@@H](C)C(F)(F)F]
34
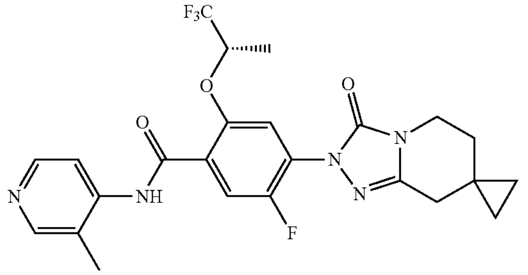 [SMILES: Cc1cnccc1NC(=O)c1cc(F)c(-n2nc3n(c2=O)CCC2(CC2)C3)cc1O[C@@H](C)C(F)(F)F]
35
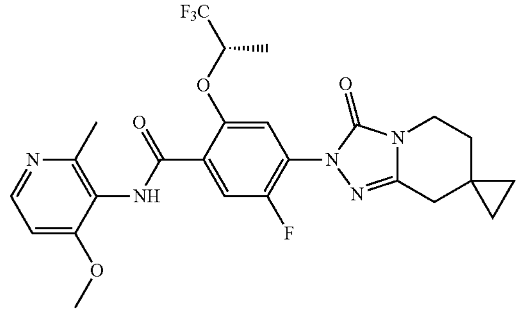 [SMILES: COc1ccnc(C)c1NC(=O)c1cc(F)c(-n2nc3n(c2=O)CCC2(CC2)C3)cc1O[C@@H](C)C(F)(F)F]
-continued
36
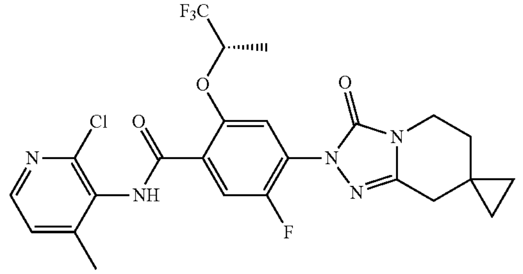 [SMILES: Cc1ccnc(Cl)c1NC(=O)c1cc(F)c(-n2nc3n(c2=O)CCC2(CC2)C3)cc1O[C@@H](C)C(F)(F)F]
37
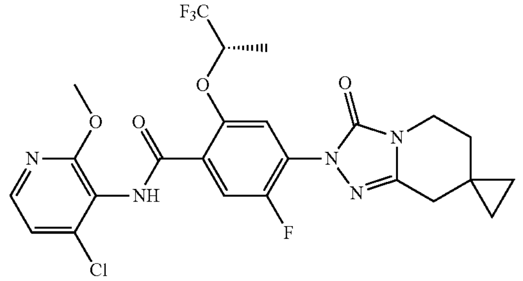 [SMILES: COc1nccc(Cl)c1NC(=O)c1cc(F)c(-n2nc3n(c2=O)CCC2(CC2)C3)cc1O[C@@H](C)C(F)(F)F]
38
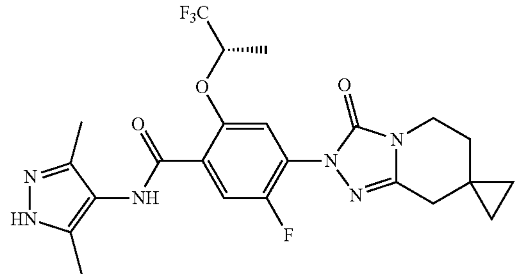 [SMILES: Cc1n[nH]c(C)c1NC(=O)c1cc(F)c(-n2nc3n(c2=O)CCC2(CC2)C3)cc1O[C@@H](C)C(F)(F)F]
39
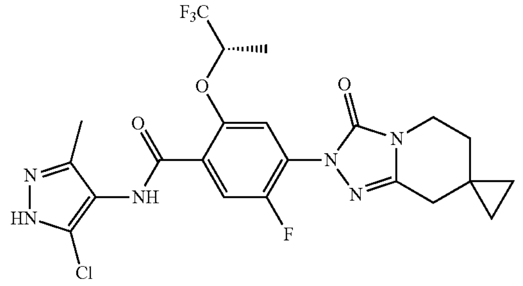 [SMILES: Cc1n[nH]c(Cl)c1NC(=O)c1cc(F)c(-n2nc3n(c2=O)CCC2(CC2)C3)cc1O[C@@H](C)C(F)(F)F]
40
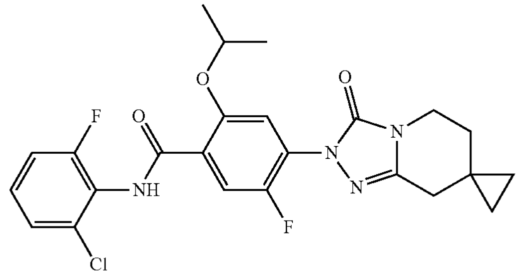 [SMILES: CC(C)Oc1cc(-n2nc3n(c2=O)CCC2(CC2)C3)c(F)cc1C(=O)Nc1c(F)cccc1Cl]

-continued
41
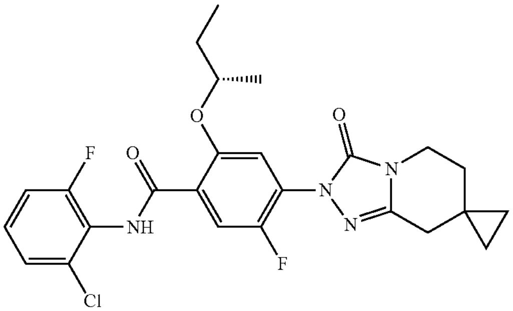 [SMILES: CC[C@H](C)Oc1cc(-n2nc3n(c2=O)CCC2(CC2)C3)c(F)cc1C(=O)Nc1c(F)cccc1Cl]
42
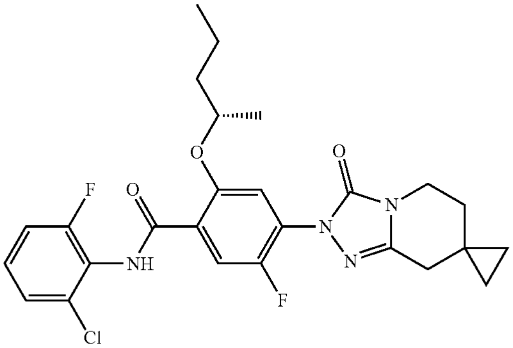 [SMILES: CCC[C@H](C)Oc1cc(-n2nc3n(c2=O)CCC2(CC2)C3)c(F)cc1C(=O)Nc1c(F)cccc1Cl]
43
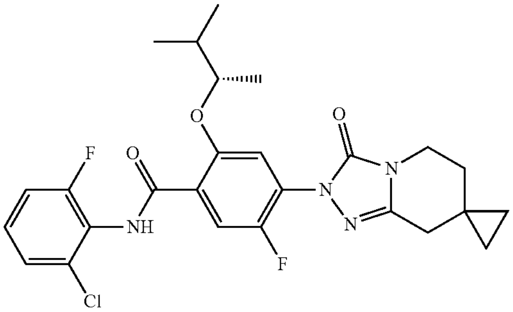 [SMILES: CC(C)[C@H](C)Oc1cc(-n2nc3n(c2=O)CCC2(CC2)C3)c(F)cc1C(=O)Nc1c(F)cccc1Cl]
44
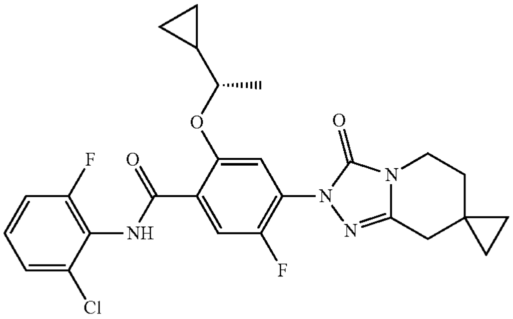 [SMILES: C[C@H](Oc1cc(-n2nc3n(c2=O)CCC2(CC2)C3)c(F)cc1C(=O)Nc1c(F)cccc1Cl)C1CC1]
45
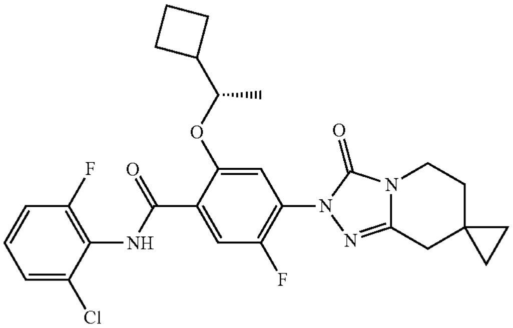 [SMILES: C[C@H](Oc1cc(-n2nc3n(c2=O)CCC2(CC2)C3)c(F)cc1C(=O)Nc1c(F)cccc1Cl)C1CCC1]
-continued
46
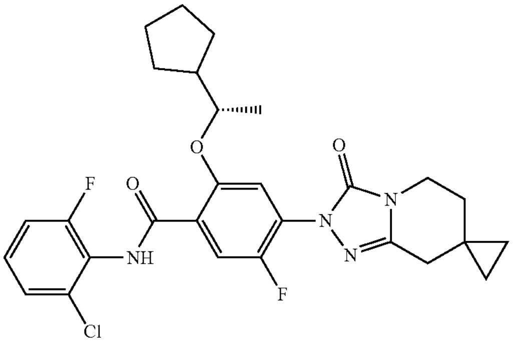 [SMILES: C[C@H](Oc1cc(-n2nc3n(c2=O)CCC2(CC2)C3)c(F)cc1C(=O)Nc1c(F)cccc1Cl)C1CCCC1]
47
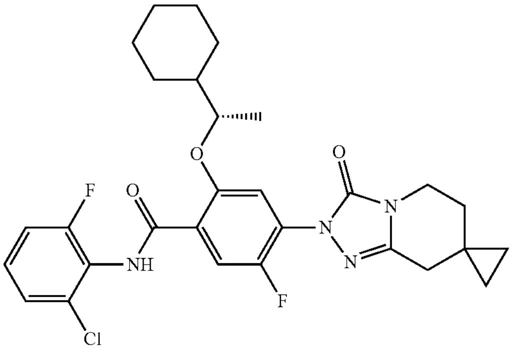 [SMILES: C[C@H](Oc1cc(-n2nc3n(c2=O)CCC2(CC2)C3)c(F)cc1C(=O)Nc1c(F)cccc1Cl)C1CCCCC1]
48
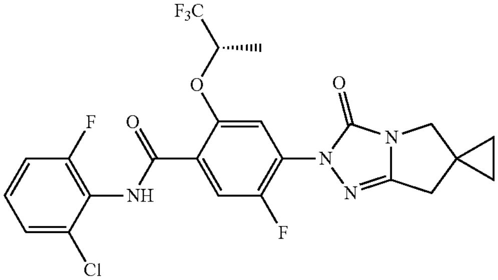 [SMILES: C[C@H](Oc1cc(-n2nc3n(c2=O)CC2(CC2)C3)c(F)cc1C(=O)Nc1c(F)cccc1Cl)C(F)(F)F]
49
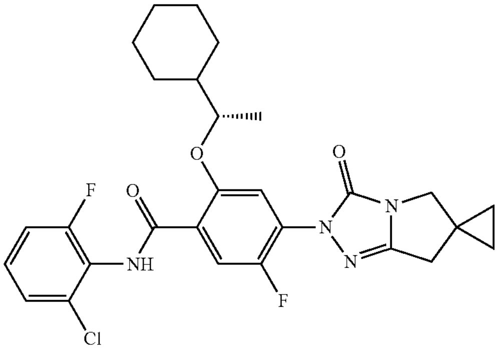 [SMILES: C[C@H](Oc1cc(-n2nc3n(c2=O)CC2(CC2)C3)c(F)cc1C(=O)Nc1c(F)cccc1Cl)C1CCCCC1]

-continued
50
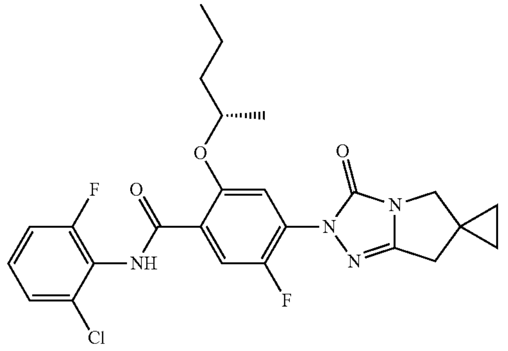 [SMILES: CCC[C@H](C)Oc1cc(-n2nc3n(c2=O)CC2(CC2)C3)c(F)cc1C(=O)Nc1c(F)cccc1Cl]
51
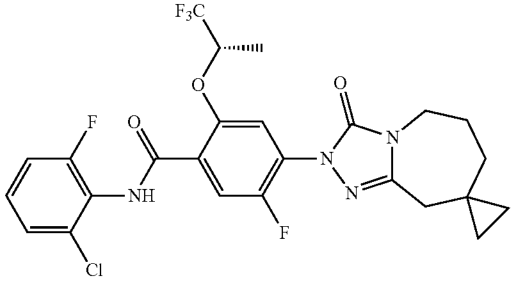 [SMILES: C[C@H](Oc1cc(-n2nc3n(c2=O)CCCC2(CC2)C3)c(F)cc1C(=O)Nc1c(F)cccc1Cl)C(F)(F)F]
52
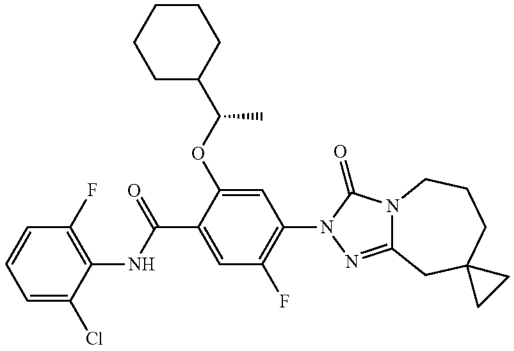 [SMILES: C[C@H](Oc1cc(-n2nc3n(c2=O)CCCC2(CC2)C3)c(F)cc1C(=O)Nc1c(F)cccc1Cl)C1CCCCC1]
53
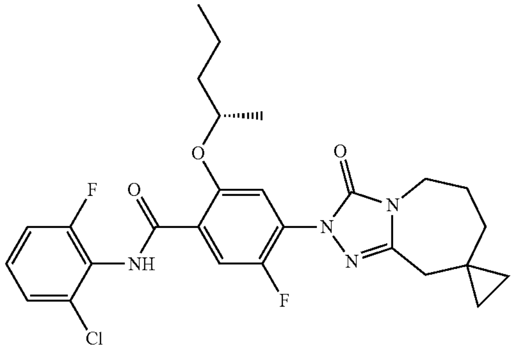 [SMILES: CCC[C@H](C)Oc1cc(-n2nc3n(c2=O)CCCC2(CC2)C3)c(F)cc1C(=O)Nc1c(F)cccc1Cl]
54
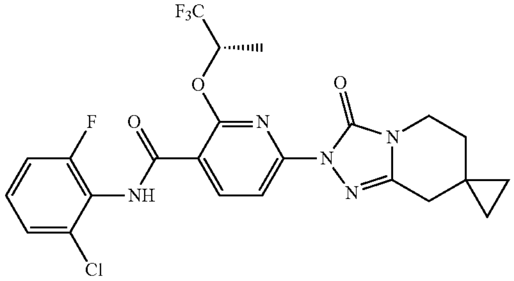
-continued
55
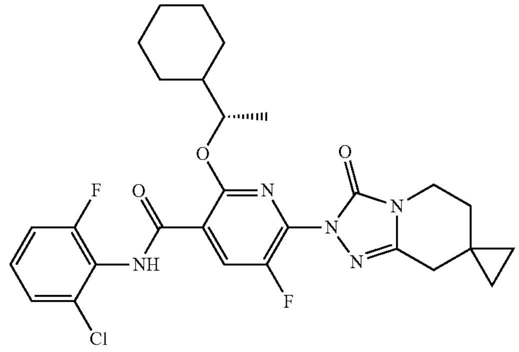 [SMILES: C[C@H](Oc1nc(-n2nc3n(c2=O)CCC2(CC2)C3)c(F)cc1C(=O)Nc1c(F)cccc1Cl)C1CCCCC1]
56
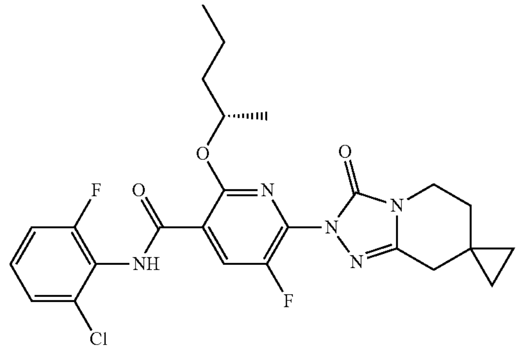 [SMILES: CCC[C@H](C)Oc1nc(-n2nc3n(c2=O)CCC2(CC2)C3)c(F)cc1C(=O)Nc1c(F)cccc1Cl]
57
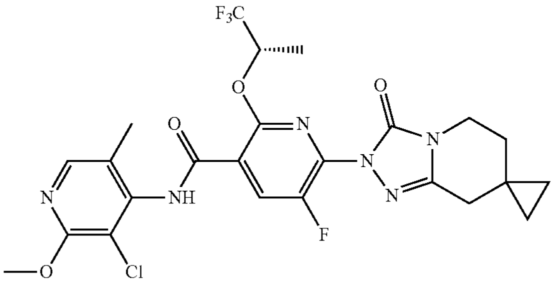 [SMILES: COc1ncc(C)c(NC(=O)c2cc(F)c(-n3nc4n(c3=O)CCC3(CC3)C4)nc2O[C@@H](C)C(F)(F)F)c1Cl]
58
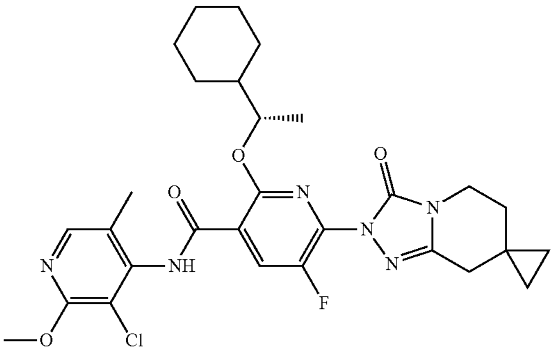

-continued

59

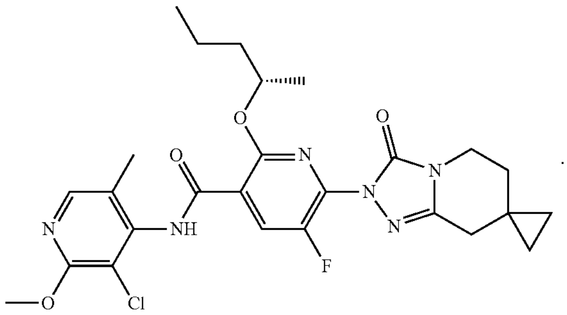

Another object of the present invention is to provide a pharmaceutical composition comprising a pharmaceutically acceptable carrier, diluent and/or excipient, and the compound of general formula (1) or the isomer, the crystalline form, the pharmaceutically acceptable salt, the hydrate or the solvate thereof of the present invention as an active ingredient.

Yet another object of the present invention is to provide use of the compound of general formula (1) or the isomer, the crystalline form, the pharmaceutically acceptable salt, the hydrate or the solvate thereof of the present invention, or the pharmaceutical composition described above in the preparation of a medicament for treating diseases associated with a tumor, wherein the tumor is preferably a solid tumor and a hematological tumor.

It should be understood that both the above general description and the following detailed description of the present invention are exemplary and explanatory, and are intended to provide further explanation of the present invention claimed.

Synthesis of Compounds

Methods for preparing the compounds of general formula (1) of the present invention are specifically described below, but these specific methods do not limit the present invention in any way.

The compounds of general formula (1) described above can be synthesized using standard synthetic techniques or well-known techniques in combination with the methods described herein. In addition, the solvents, temperatures and other reaction conditions mentioned herein may vary. Starting materials for the synthesis of the compounds can be obtained synthetically or commercially. The compounds described herein and other related compounds with different substituents can be synthesized using well-known techniques and starting materials, including the methods found in March, Advanced Organic Chemistry, $4^{th}$ Ed., (Wiley 1992); Carey and Sundberg, Advanced Organic Chemistry, $4^{th}$ Ed., Vols. A and B (Plenum 2000, 2001); and Green and Wuts, Protective Groups in Organic Synthesis, $3^{rd}$ Ed., (Wiley 1999). General methods for preparing the compounds can be modified by using appropriate reagents and conditions for introducing different groups into the molecular formulas provided herein.

In one aspect, the compounds described herein are prepared according to methods well known in the art. However, the conditions of the methods, such as reactants, solvents, bases, the amount of the compounds used, reaction temperature and time required for the reaction are not limited to the following explanation. The compounds of the present invention can also be conveniently prepared by optionally combining various synthetic methods described herein or known in the art, and such combinations can be easily determined by those skilled in the art to which the present invention pertains. In one aspect, the present invention further provides a method for preparing the compound of general formula (1), wherein the compound of general formula (1) can be prepared using method A or method B below:

Method A includes the following steps: firstly, reacting compound A1 with compound A2 under strong alkaline conditions to give compound A3, further reacting the compound A3 with compound A4 under the action of a strong alkali to give compound A5, and subjecting the compound A5 and compound A6 to a coupling reaction to give target compound A7.

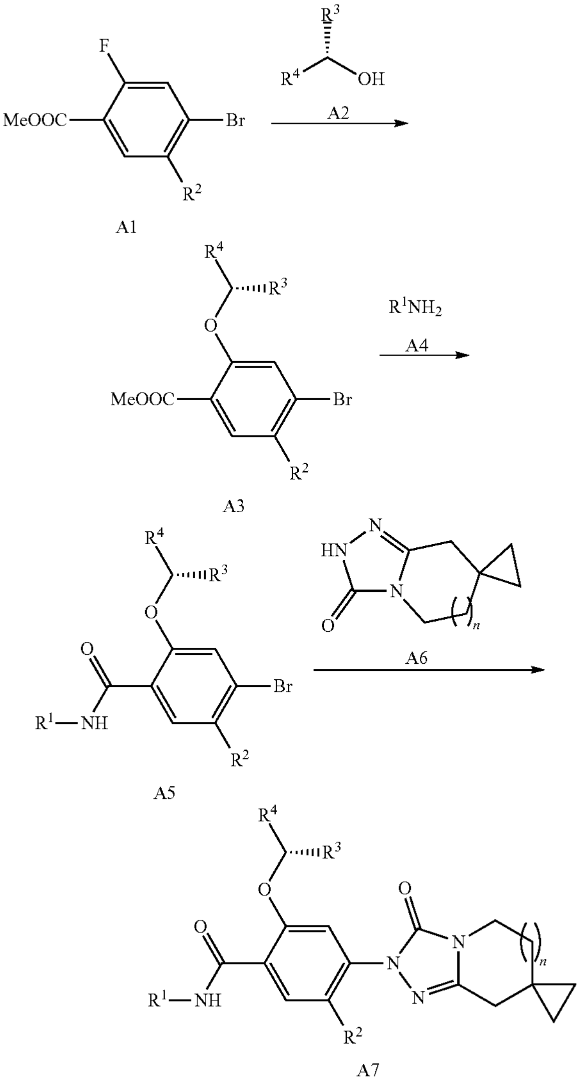

In the above reaction equation, n, $R^1$, $R^2$, $R^3$ and $R^4$ are as defined above.

Method B includes the following steps: firstly, subjecting the carboxyl of compound B1 to a chlorination reaction to give acyl chloride compound B2, further reacting the compound B2 with isopropanol under the action of a strong alkali to give compound B3, reacting the compound B3 with the compound A6 under alkaline conditions to give compound B4, reacting the compound B4 under strong alkaline conditions and then reacting it with the compound A2 to give compound B5, and reacting the compound B5 with a proper starting material A4 to give target compound B6.

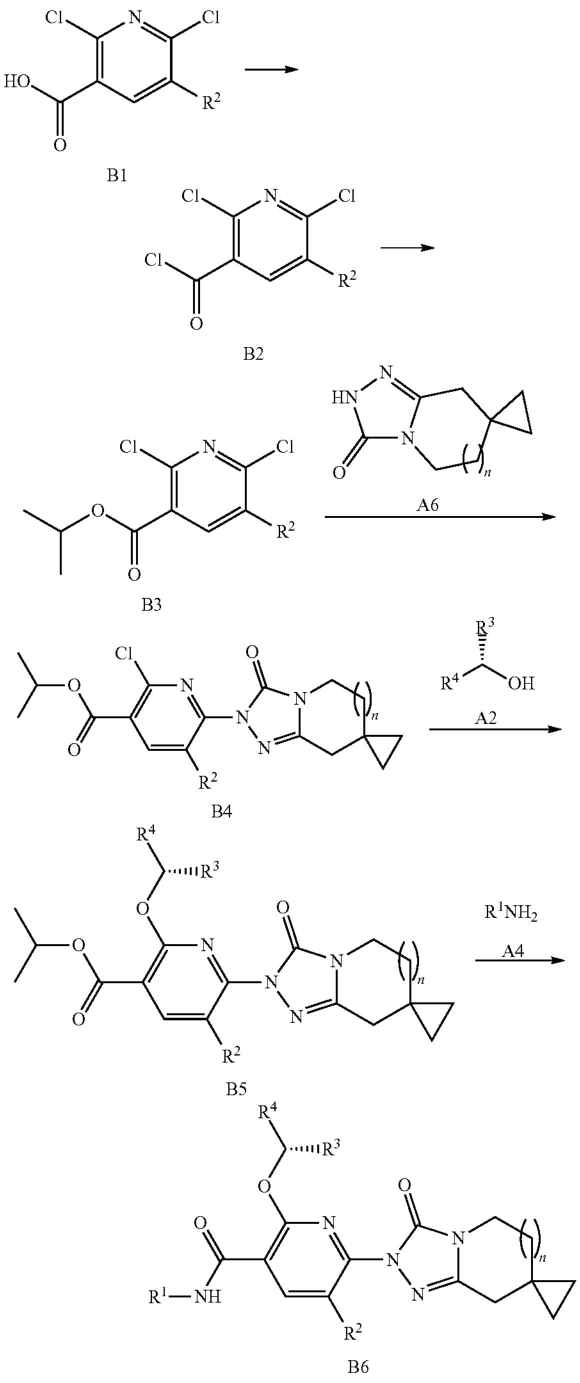

B1

B2

B3

B4

B5

B6

In the above reaction equation, n, $R^1$, $R^2$, $R^3$ and $R^4$ are as defined above.

Further Forms of Compounds

"Pharmaceutically acceptable" herein refers to a substance, such as a carrier or diluent, which will not lead to loss of biological activity or properties of a compound and is relatively non-toxic. For example, when an individual is given a substance, the substance will not cause undesired biological effects or interact with any component contained therein in a deleterious manner.

The term "pharmaceutically acceptable salt" refers to a form of a compound that does not cause significant irritation to the organism receiving the administration or eliminate the biological activity and properties of the compound. In certain specific aspects, the pharmaceutically acceptable salt is obtained by subjecting the compound of general formula (1) to a reaction with acids, e.g., inorganic acids such as hydrochloric acid, hydrobromic acid, hydrofluoric acid, sulfuric acid, phosphoric acid, nitric acid, carbonic acid and the like; organic acids such as formic acid, acetic acid, propionic acid, oxalic acid, trifluoroacetic acid, malonic acid, succinic acid, fumaric acid, maleic acid, lactic acid, malic acid, tartaric acid, citric acid, picric acid, methanesulfonic acid, benzenesulfonic acid, p-toluenesulfonic acid and the like; and acidic amino acids such as aspartic acid, glutamic acid and the like.

It should be understood that references to pharmaceutically acceptable salts include solvent addition forms or crystalline forms, especially solvates or polymorphs. A solvate contains either stoichiometric or non-stoichiometric amount of solvent and is selectively formed during crystallization in a pharmaceutically acceptable solvent such as water and ethanol. Hydrates are formed when the solvent is water, or alcoholates are formed when the solvent is ethanol. The solvates of the compound of general formula (1) are conveniently prepared or formed according to the methods described herein. For example, hydrates of the compound of general formula (1) are conveniently prepared by recrystallization in a mixed solvent of water/organic solvent, wherein the organic solvent used includes, but is not limited to, tetrahydrofuran, acetone, ethanol or methanol. Furthermore, the compounds described herein may be present in either a non-solvated form or a solvated form. In general, the solvated forms are considered equivalent to the non-solvated forms for purposes of the compounds and methods provided herein.

In other specific examples, the compound of general formula (1) is prepared in different forms including, but not limited to, amorphous, pulverized and nanoparticle forms. In addition, the compound of general formula (1) includes crystalline forms, and may also be polymorphs. Polymorphs include different lattice arrangements of the same elements of a compound. The polymorphs generally have different X-ray diffraction spectra, infrared spectra, melting points, density, hardness, crystalline forms, optical and electrical properties, stability and solubility. Different factors such as a recrystallization solvent, crystallization rate, and storage temperature may lead to a single dominant crystalline form.

In another aspect, the compound of general formula (1) may have a chiral center and/or axial chirality, and thus may be present in the form of a racemate, a racemic mixture, a single enantiomer, a diastereomeric compound, a single diastereomer and a cis-trans isomer. Each chiral center or axial chirality will independently produce two optical isomers, and all possible optical isomers, diastereomeric mixtures, and pure or partially pure compounds are included within the scope of the present invention. The present invention is meant to include all such isomeric forms of these compounds.

The compound of the present invention may contain unnatural proportions of atomic isotopes at one or more of the atoms that constitute the compound. For example, the compound may be labeled with radioactive isotopes, such as tritium (3H), iodine-125 ($^{125}I$), and C-14 ($^{14}C$). For another example, deuterium can be used to substitute a hydrogen atom to form a deuterated compound. The bond formed by deuterium and carbon is stronger than that formed by ordinary hydrogen and carbon. Compared with an undeuterated medicament, the deuterated medicament generally has the advantages of reduced toxic and side effects, increased pharmaceutical stability, enhanced efficacy, prolonged pharmaceutical in vivo half-life and the like. All isotopic variations of the compound of the present invention, whether radioactive or not, are contained within the scope of the present invention.

Terminology

Unless otherwise stated, the terms used in the present application, including those in the specification and claims, are defined as follows. It must be noted that in the specification and the appended claims, the singular forms "a" and "an" include plural meanings unless clearly indicated otherwise. Unless otherwise stated, conventional methods for mass spectrometry, nuclear magnetic resonance spectroscopy, HPLC, protein chemistry, biochemistry, recombinant DNA techniques and pharmacology are used. As used herein, "or" or "and" refers to "and/or" unless otherwise stated.

Unless otherwise specified, "alkyl" refers to a saturated aliphatic hydrocarbon group, including linear and branched groups containing 1 to 6 carbon atoms. Lower alkyl groups containing 1 to 4 carbon atoms, such as methyl, ethyl, propyl, 2-propyl, n-butyl, isobutyl, or tert-butyl, are preferred. As used herein, "alkyl" includes unsubstituted and substituted alkyl, particularly alkyl substituted with one or more halogens. Preferred alkyl is selected from $CH_3$, $CH_3CH_2$, $CF_3$, $CHF_2$, $CF_3CH_2$, $CF_3(CH_3)CH$, $^{i}$Pr, $^{n}$Pr, $^{i}$Bu, $^{n}$Bu or $^{t}$Bu.

Unless otherwise specified, "cycloalkyl" refers to a non-aromatic hydrocarbon ring system (monocyclic, bicyclic or polycyclic), and partially unsaturated cycloalkyl may be referred to as "cycloalkenyl" if the carbocyclic ring contains at least one double bond, or "cycloalkynyl" if the carbocyclic ring contains at least one triple bond. Cycloalkyl may include monocyclic or polycyclic groups and spiro rings (e.g., having 2, 3 or 4 fused rings). In some embodiments, cycloalkyl is monocyclic. In some embodiments, cycloalkyl is monocyclic or bicyclic. The ring carbon atoms of cycloalkyl may optionally be oxidized to form an oxo or sulfido group. Cycloalkyl further includes cycloalkylene. In some embodiments, cycloalkyl contains 0, 1 or 2 double bonds. In some embodiments, cycloalkyl contains 1 or 2 double bonds (partially unsaturated cycloalkyl). In some embodiments, cycloalkyl may be fused to aryl, heteroaryl, cycloalkyl and heterocycloalkyl. In some embodiments, cycloalkyl may be fused to aryl, cycloalkyl and heterocycloalkyl. In some embodiments, cycloalkyl may be fused to aryl and heterocycloalkyl. In some embodiments, cycloalkyl may be fused to aryl and cycloalkyl. Examples of cycloalkyl include cyclopropyl, cyclobutyl, cyclopentyl, cyclohexyl, cycloheptyl, cyclopentenyl, cyclohexenyl, cyclohexadienyl, cycloheptatrienyl, norcamphanyl, norpinanyl, norcarnyl, bicyclo[1.1.1]pentyl, bicyclo[2.1.1]hexyl and the like.

Unless otherwise specified, "alkoxy" refers to an alkyl group that bonds to the rest of the molecule through an ether oxygen atom. Representative alkoxy groups are those having 1-6 carbon atoms, such as methoxy, ethoxy, propoxy, isopropoxy, butoxy, isobutoxy, sec-butoxy, and tert-butoxy. As used herein, "alkoxy" includes unsubstituted and substituted alkoxy, particularly alkoxy substituted with one or more halogens. Preferred alkoxy is selected from $OCH_3$, $OCF_3$, $CHF_2O$, $CF_3CH_2O$, $^{n-}$PrO, $^{n-}$PrO, $^{i-}$BuO, $^{n-}$BuO, or $^{t-}$BuO.

Unless otherwise specified, "aryl" refers to an aromatic hydrocarbon group, which is monocyclic or polycyclic; for example, a monocyclic aryl ring may be fused to one or more carbocyclic aromatic groups. Examples of aryl include, but are not limited to, phenyl, naphthyl, and phenanthryl.

Unless otherwise specified, "heteroaryl" refers to an aromatic group containing one or more heteroatoms (O, S, or N), and the "heteroaryl" is monocyclic or polycyclic. For example, a monocyclic heteroaryl ring is fused to one or more carbocyclic aromatic groups or other monocyclic heterocycloalkyl groups. Examples of heteroaryl include, but are not limited to, pyridinyl, pyridazinyl, imidazolyl, pyrimidinyl, pyrazolyl, triazolyl, pyrazinyl, quinolinyl, isoquinolinyl, furanyl, thienyl, isoxazolyl, thiazolyl, oxazolyl, isothiazolyl, pyrrolyl, indolyl, benzimidazolyl, benzofuranyl, benzothiazolyl, benzothienyl, benzoxazolyl, benzopyridinyl, pyrrolopyrimidinyl, 1H-pyrrolo[3,2-b]pyridinyl, 1H-pyrrolo[2,3-c]pyridinyl, 1H-pyrrolo[3,2-c]pyridinyl, 1H-pyrrolo[2,3-b]pyridinyl,

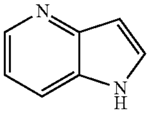
,
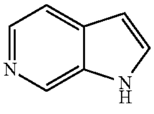
,
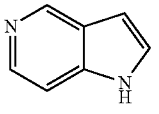
, and
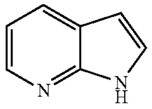
.

Unless otherwise specified, "halogen" (or halo) refers to fluorine, chlorine, bromine or iodine. The term "halo" (or "halogenated") before a group name indicates that the group is partially or fully halogenated, that is, substituted in any combination with F, Cl, Br or I, preferably with F or Cl.

"Optional" or "optionally" means that the subsequently described event or circumstance may, but does not necessarily, occur, and the description includes instances where the event or circumstance occurs and instances where the event or circumstance does not occur.

The term "membered ring" includes any cyclic structure. The term "membered" is intended to refer to the number of backbone atoms that form a ring. For example, cyclohexyl, pyridinyl, pyranyl and thiopyranyl are six-membered rings, and cyclopentyl, pyrrolyl, furanyl and thienyl are five-membered rings.

The term "moiety" refers to a specific portion or functional group of a molecule. A chemical moiety is generally considered to be a chemical entity contained in or attached to a molecule. Unless otherwise stated, the absolute configuration of a stereogenic center is represented by a wedged solid bond ( ) and a wedged dashed bond ( ), and the relative configuration of a stereogenic center is represented by a straight solid bond ( ) and a straight dashed bond ( ). A wavy line ( ) represents a wedged solid bond ( ) or a wedged dashed bond ( ), or a wavy line ( ) represents a straight solid bond ( ) or a straight dashed bond ( ).

Unless otherwise stated, a single bond or a double bond is represented by .

Specific Pharmaceutical and Medical Terminology

The term "acceptable", as used herein, means that a formulation component or an active ingredient does not unduly and adversely affect a general therapeutic target's health.

The terms "treatment", "treatment course", and "therapy", as used herein, include alleviating, inhibiting, or ameliorating a symptom or condition of a disease; inhibiting the development of complications; ameliorating or preventing underlying metabolic syndrome; inhibiting the development of a disease or symptom, e.g., controlling the progression of a disease or condition; alleviating a disease or symptom; leading to disease or symptom regression; and alleviating a complication caused by a disease or symptom, or preventing or treating a sign caused by a disease or symptom. As used herein, a compound or pharmaceutical composition, when administered, can ameliorate a disease, symptom, or condition, which particularly refers to ameliorating the severity, delaying the onset, slowing the progression, or reducing the duration of the disease. Fixed or temporary administration, or continuous or intermittent administration, may be attributed to or associated with the administration.

"Active ingredient" refers to the compound of general formula (1), and pharmaceutically acceptable inorganic or organic salts of the compound of general formula (1). The compound of the present invention may contain one or more asymmetric centers (chiral center or axial chirality) and thus occur in the form of a racemate, a racemic mixture, a single enantiomer, a diastereomeric compound and a single diastereomer. Asymmetric centers that may be present depend on the nature of the various substituents on the molecule. Each of such asymmetric centers will independently produce two optical isomers, and all possible optical isomers, diastereomeric mixtures and pure or partially pure compounds are included within the scope of the present invention. The present invention is meant to include all such isomeric forms of these compounds.

The terms such as "compound", "composition", "agent", or "medicine or medicament" are used interchangeably herein and all refer to a compound or composition that, when administered to an individual (human or animal), is capable of inducing a desired pharmacological and/or physiological response by local and/or systemic action.

The term "administered, administering, or administration" refers herein to the direct administration of the compound or composition, or the administration of a prodrug, derivative, analog, or the like of the active compound.

Although the numerical ranges and parameters defining the broad scope of the present invention are approximations, the related numerical values set forth in the specific examples have been presented herein as precisely as possible. Any numerical value, however, inherently contains a standard deviation necessarily resulting from certain methods of testing. Herein, "about" generally means that the actual value is within a particular value or range ±10%, 5%, 1%, or 0.5%. Alternatively, the term "about" indicates that the actual numerical value falls within the acceptable standard error of a mean, as considered by those skilled in the art. All ranges, quantities, numerical values, and percentages used herein (e.g., to describe an amount of a material, a length of time, a temperature, an operating condition, a quantitative ratio, and the like) are to be understood as being modified by the word "about", except in the experimental examples or where otherwise explicitly indicated. Accordingly, unless otherwise contrarily stated, the numerical parameters set forth in the specification and the appended claims are all approximations that may vary as desired. At least, these numerical parameters should be understood as the significant digits indicated or the numerical values obtained using conventional rounding rules.

Unless otherwise defined in the specification, the scientific and technical terms used herein have the same meaning as commonly understood by those skilled in the art. Furthermore, nouns in their singular forms used in the specification encompass their plural forms, unless contradicted by context; nouns in their plural forms used also encompass their singular forms.

Therapeutic Use

The present invention provides a method for treating a disease, including but not limited to a condition involving DHODH (e.g., cancer), with the compound of general formula (1) or the pharmaceutical composition of the present invention.

In some embodiments, a method for treating cancer is provided, the method including administering to an individual in need thereof an effective amount of any aforementioned pharmaceutical composition including the compound of structural general formula (1). In other embodiments, the cancer is a hematologic cancer and a solid tumor, including but not limited to, leukemia, breast cancer, lung cancer, pancreatic cancer, colon cancer, bladder cancer, brain cancer, urothelial cancer, prostate cancer, liver cancer, ovarian cancer, head and neck cancer, gastric cancer, mesothelioma or all cancer metastases.

Route of Administration

The compound and the pharmaceutically acceptable salt thereof of the present invention can be made into various formulations including a safe and effective amount of the compound or the pharmaceutically acceptable salt thereof of the present invention, and a pharmaceutically acceptable excipient or carrier, wherein the "safe and effective amount" means that the amount of the compound is sufficient to significantly improve the condition without causing serious adverse effects. The safe and effective amount of the compound is determined according to the age, condition, course of treatment, and other specific conditions of a treated subject.

The "pharmaceutically acceptable excipient or carrier" refers to one or more compatible solid or liquid fillers or gel substances that are suitable for human use and must be of sufficient purity and sufficiently low toxicity. "Compatible" herein means that the components of the composition are capable of intermixing with the compound of the present invention and with each other, without significantly diminishing the pharmaceutical efficacy of the compound. Examples of pharmaceutically acceptable excipients or carriers include cellulose and derivatives thereof (e.g., sodium carboxymethylcellulose, sodium ethylcellulose, or cellulose acetate), gelatin, talc, solid lubricants (e.g., stearic acid or magnesium stearate), calcium sulfate, vegetable oil (e.g., soybean oil, sesame oil, peanut oil, or olive oil), polyols (e.g., propylene glycol, glycerol, mannitol, or sorbitol), emulsifiers (e.g., Tween®), wetting agents (e.g., sodium lauryl sulfate), colorants, flavoring agents, stabilizers, antioxidants, preservatives, pyrogen-free water, etc.

When the compound of the present invention is administered, it may be administered orally, rectally, parenterally (intravenously, intramuscularly, or subcutaneously), or topically.

Solid dosage forms for oral administration include capsules, tablets, pills, pulvises, and granules. In these solid dosage forms, the active compound is mixed with at least one conventional inert excipient (or carrier), such as sodium citrate or dicalcium phosphate, or with the following ingredients: (a) fillers or extenders, such as starch, lactose, sucrose, glucose, mannitol, and silicic acid; (b) binders, such as hydroxymethyl cellulose, alginate, gelatin, polyvinylpyrrolidone, sucrose, and acacia; (c) humectants, such as glycerol; (d) disintegrants, such as agar, calcium carbonate, potato or tapioca starch, alginic acid, certain complex silicates, and sodium carbonate; (e) solution retarders, such as paraffin; (f) absorption accelerators, such as quaternary ammonium compounds; (g) wetting agents, such as cetyl alcohol and glycerol monostearate; (h) adsorbents, such as kaolin; and (i) lubricants, such as talc, calcium stearate, magnesium stearate, solid polyethylene glycol and sodium lauryl sulfate, or mixtures thereof. In the case of capsules, tablets, and pills, the dosage forms may further include buffers.

Solid dosage forms such as tablets, dragees, capsules, pills, and granules can be prepared using coatings and shells such as enteric coatings and other materials well known in the art. They may include opacifying agents, and the active compound or compound in such a composition may be released in a certain part of the digestive tract in a delayed manner. Examples of embedding components that can be used are polymeric substances and wax-based substances. If necessary, the active compound can also be in microcapsule form with one or more of the above-mentioned excipients.

Liquid dosage forms for oral administration include pharmaceutically acceptable emulsions, solutions, suspensions, syrups, and elixirs. In addition to the active compound, the liquid dosage form may include inert diluents commonly used in the art, such as water or other solvents, solubilizers and emulsifiers, for example, ethanol, isopropanol, ethyl carbonate, ethyl acetate, propylene glycol, 1,3-butanediol, dimethylformamide, and oils, especially cottonseed oil, peanut oil, corn germ oil, olive oil, castor oil and sesame oil, or mixtures of these substances.

Besides such inert diluents, the composition may further include adjuvants, such as wetting agents, emulsifiers, suspending agents, sweeteners, flavoring agents, and perfuming agents.

In addition to the active compound, suspensions may include suspending agents, such as ethoxylated isostearyl alcohols, polyoxyethylene sorbitol and sorbitan esters, microcrystalline cellulose, aluminum methylate and agar, or mixtures of these substances.

Compositions for parenteral injection may include physiologically acceptable sterile aqueous or anhydrous solutions, dispersions, suspensions or emulsions, and sterile powders for redissolving into sterile injectable solutions or dispersions. Suitable aqueous and non-aqueous carriers, diluents, solvents, or excipients include water, ethanol, polyols, and suitable mixtures thereof.

Dosage forms for topical administration of the compound of the present invention include ointments, pulvises, patches, sprays, and inhalants. The active ingredient is mixed under sterile conditions with a physiologically acceptable carrier and any preservatives, buffers or propellants that may be required if necessary.

The compound of the present invention may be administered alone or in combination with other pharmaceutically acceptable compounds. When the pharmaceutical composition is used, a safe and effective amount of the compound of the present invention is administered to a mammal (such as a human) to be treated, wherein the dose of administration is a pharmaceutically effective dose. For a human of 60 kg, the daily dose of administration is usually 1-2000 mg, preferably 50-1000 mg. In determining a specific dose, such factors as the route of administration, the health condition of the patient and the like will also be considered, which are well known to skilled physicians.

The above features mentioned in the present invention or those mentioned in the examples may be combined arbitrarily. All the features disclosed in this specification may be used with any composition form and the various features disclosed in this specification may be replaced with any alternative features that provide the same, equivalent, or similar pharmaceutical composition. Thus, unless otherwise specified, the features disclosed herein are merely general examples of equivalent or similar features.

DETAILED DESCRIPTION

Various specific aspects, features, and advantages of the compounds, methods, and pharmaceutical compositions described above will be set forth in detail in the following description, which will make the content of the present invention very clear. It should be understood that the detailed description and examples below describe specific examples for reference only. After reading the description of the present invention, those skilled in the art can make various changes or modifications to the present invention, and such equivalents also fall within the scope of the present application defined herein.

In all the examples, $^1H$-NMR spectra were recorded with a Varian Mercury 400 nuclear magnetic resonance spectrometer, and chemical shifts are represented by δ (ppm); silica gel for separation was 200-300 mesh silica gel if not specified, and the ratio of the eluents was a volume ratio.

The following abbreviations are used in the present invention: $AlMe_3$ represents trimethylaluminum; Ar represents argon; $CDCl_3$ represents deuterated chloroform; $(COCl)_2$ represents oxalyl chloride; $Cs_2CO_3$ represents cesium carbonate; DCM represents dichloromethane; dioxane represents 1,4-dioxane; DMF represents N,N-dimethylformamide; DMSO represents dimethyl sulfoxide; EA or EtOAc represents ethyl acetate; h represents hour; IPA represents isopropanol; KF represents potassium fluoride; KHMDS represents potassium bis(trimethylsilyl) amide; LC-MS represents liquid chromatography-mass spectrometry; $Me_3OBF_4$ represents trimethyloxonium tetrafluoroborate; MeOH represents methanol; mL represents milliliter; min represents minute; MS represents mass spectrometry; NaH represents sodium hydride; $Na_2SO_4$ represents sodium sulfate; NMR represents nuclear magnetic resonance; $Pd_2(dba)_3$ represents tris(dibenzylideneacetone)dipalladium(0); PE represents petroleum ether; py represents pyridine; Xantphos represents 4,5-bis(diphenylphosphino)-9,9-dimethylxanthene; THE represents tetrahydrofuran; Tol represents methylbenzene.

Example 1. Synthesis of (S)—N-(2-chloro-6-fluorophenyl)-5-fluoro-4-(3'-oxo-5',6'-dihydro-3'H-spiro[cyclopropane-1,7-[1,2,4]triazolo[4,3-α]pyridin]-2'(8'H)-yl)-2-((1,1,1-trifluoropropan-2-yl)oxy)benzamide (Compound 1)

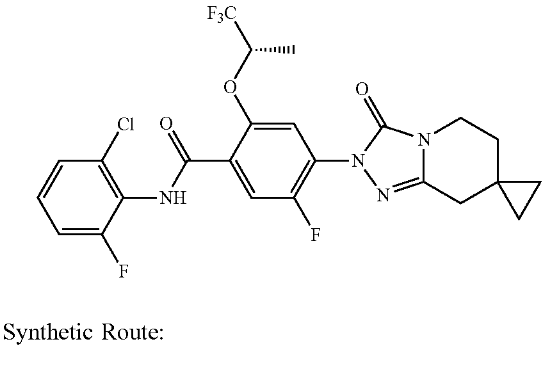

1

Synthetic Route:

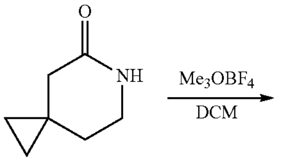

1-1

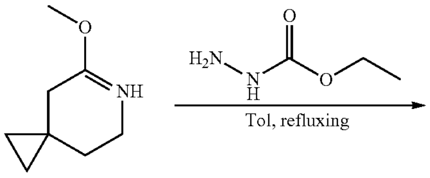

1-2

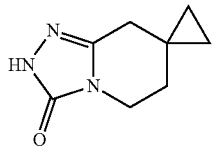

1-3

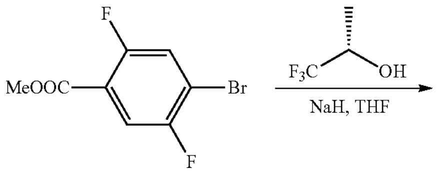

1-4

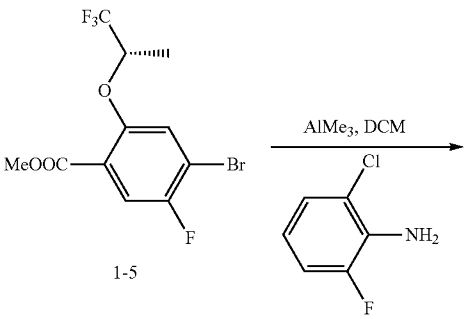

1-5

-continued

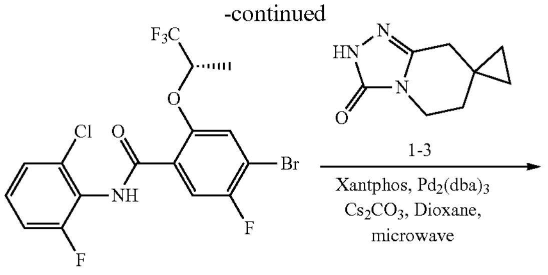

1-6

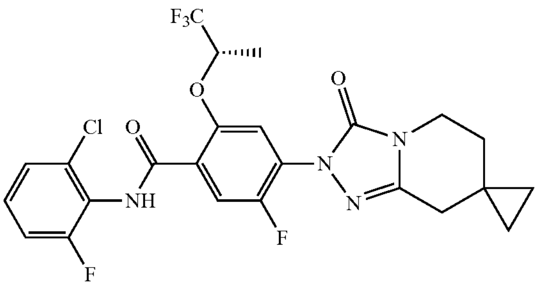

1

Step 1: Synthesis of Compound 1-2

1-1 (4.6 g, 36.75 mmol) and DCM (100 mL) were added to a 250 mL single-neck flask. After the mixed solution was purged with Ar, $Me_3OBF_4$ (8.2 g, 55.12 mmol) was added. The mixed solution was stirred at room temperature for 20 h under Ar atmosphere, then $Me_3OBF_4$ (2.73 g, 28.46 mmol) was supplemented, and the resulting mixture was stirred for reaction at room temperature for another 20 h. After the basic completion of the reaction as detected by LC-MS, the mixed solution was quenched with ice water (50 mL), the pH was adjusted to 7-8 with saturated sodium bicarbonate, liquid separation was carried out, and the aqueous phase was extracted with DCM (50 mL). The organic phases were combined and washed with saturated sodium chloride solution (50 mL), dried over anhydrous $Na_2SO_4$, filtered, and concentrated to give a crude product 1-2 as a yellow-brown solid (3.6 g, 70.4% yield), ESI-MS m/z: 140.1 $[M+H]^+$.

Step 2: Synthesis of Compound 1-3

1-2 (3.6 g, 25.86 mmol) and methylbenzene (80 mL) were added to a 250 mL single-neck flask. After the mixed solution was purged with Ar, ethyl carbazate (4.04 g, 38.79 mmol) was added, and the mixed solution was heated to 120° C. under Ar atmosphere and stirred for reaction for 40 h. After the completion of the reaction as detected by LC-MS, the mixed solution was concentrated to dryness, and the residue was purified by column chromatography (DCM:MeOH=100:0 to 100:1 to 60:1 to 20:1) to give a product 1-3 as a white solid (1.77 g, 41.4% yield), ESI-MS m/z: 166.1 $[M+H]^+$.

Step 3: Synthesis of Compound 1-5

(S)-1,1,1-trifluoropropan-2-ol (2.726 g, 23.90 mmol) and anhydrous THE (30 mL) were added to a 100 mL three-necked flask. The mixed solution was cooled to −5° C. to −10° C. in an ice salt bath under Ar atmosphere, and NaH (860 mg, 60%, 21.51 mmol) was added in batches. After the addition, the mixed solution was stirred at a constant temperature for 1 h. Then 1-4 (3.0 g, 11.95 mmol) was added, the ice bath was removed, and the mixed solution was stirred for reaction at room temperature for about 3 h. After the completion of the reaction as detected by LC-MS, EA (20 mL) was added to the mixed solution, ice water (20 mL) was added for quenching the reaction, the mixed solution was stirred, liquid separation was carried out, and the aqueous phase was extracted with EA (20 mL). The organic phases were combined, washed with saturated sodium chloride solution, dried over anhydrous $Na_2SO_4$, filtered, and concentrated to give a product 1-5 as a colorless transparent oil (2.99 g, 72.5% yield), ESI-MS m/z: 345.0/347.0 $[M+H]^+$.

Step 4: Synthesis of Compound 1-6

2-Chloro-6-fluoroaniline (6.11 g, 42.0 mmol) and anhydrous DCM (60 mL) were added to a 250 mL three-necked flask. After the mixed solution was purged with Ar, trimethylaluminum (42 mL, 1 M in n-heptane, 42 mmol) was added dropwise at room temperature. After dropwise addition, the mixed solution was stirred at room temperature for 2 h. Then 1-5 (3.62 g, 10.5 mmol) was added. After being purged with Ar, the mixed solution was heated to 50° C., and stirred for reaction for 3 h. After the completion of the reaction as detected by LC-MS, the reaction solution was slowly poured into saturated ammonium chloride solution (100 mL) in an ice bath. After the mixed solution was stirred for 30 min in an ice bath, liquid separation was carried out, and the aqueous phase was extracted three times with DCM (100 mL×3). The organic phases were combined, washed with saturated sodium chloride solution (100 mL), and concentrated, and the residue was purified by column chromatography (PE:EA=40:0 to 40:1 to 20:1 to 10:1) to give a product 1-6 as a yellow-brown colloidal solid (4.46 g, 90.1% yield), ESI-MS m/z: 458.0 $[M+H]^+$.

Step 5: Synthesis of Compound 1

1-6 (500 mg, 1.09 mmol), 1-3 (234 mg, 1.42 mmol), $Cs_2CO_3$ (710 mg, 2.18 mmol), Xantphos (378 mg, 0.654 mmol), and dioxane (10 mL) were added to a 30 mL microwave reactor. After the mixed solution was purged with Ar, $Pd_2(dba)_3$ (300 mg, 0.327 mmol) was added, and the mixture was stirred for reaction under microwave at a constant temperature of 110° C. for 15 h. After the completion of the reaction as detected by LC-MS, the mixed solution was filtered, the filter cake was rinsed with EA (about 10 mL), the filtrate was concentrated, the residue was purified by column chromatography (PE:EA=4:0 to 4:1 to 3:1 to 2:1) to give an impure product (about 400 mg), and then the impure product was purified by prep-HIPLC to give a product, compound 1, as a white foamy solid (340 mg, 57.500 yield, HIPLC>99%).

$^1H$ NMR (400 MHz, $CDCl_3$) δ: 9.01 (s, 1H), 8.17 (d, J=11.6 Hz, 1H), 7.51 (d, J=5.6 Hz, 1H), 7.28 (dt, J=8.4, 1.3 Hz, 1H), 7.25-0.20 (in, 1H), 7.12 (ddd, J=9.6, 8.2, 1.6 Hz, 1H), 4.94 (p, J=6.2 Hz, 1H), 3.78 (t, J=6.2 Hz, 2H), 2.67 (s, 2H), 1.82 (t, J=6.1 Hz, 2H), 1.65 (d, J=6.8 Hz, 3H), 0.61 (s, 4H), ESI-MS m/z: 543.2 $[M+H]^+$.

Examples 2-53: Synthesis of Compounds 2-53

The target compounds 2-53 were obtained according to a similar synthesis method as in Example 1 using different starting materials.

TABLE 1

| Compound | Compound structure | $[M + H]^+$ |
| --- | --- | --- |
| 2 | 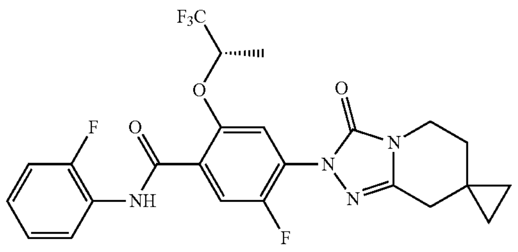 | 509.2 |
| 3 | 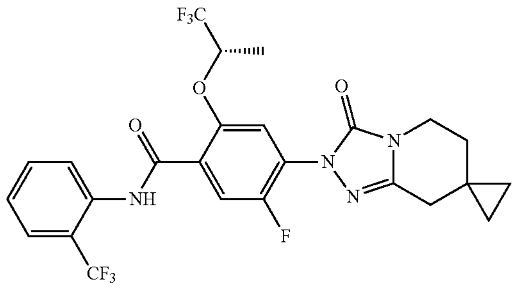 | 559.2 |
| 4 | 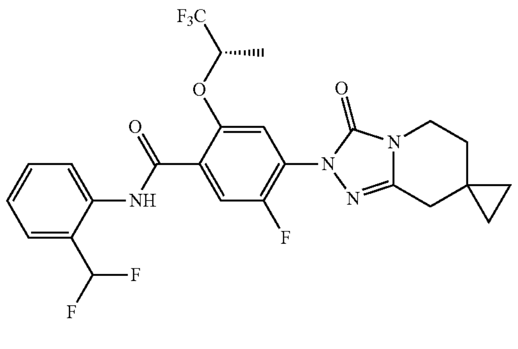 | 541.2 |

TABLE 1-continued
| Compound | Compound structure | [M + H]+ |
| --- | --- | --- |
| 5 | 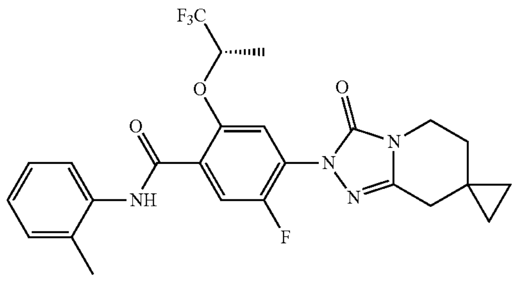 | 505.2 |
| 6 | 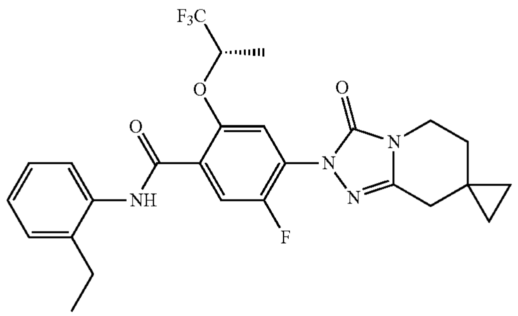 | 519.2 |
| 7 | 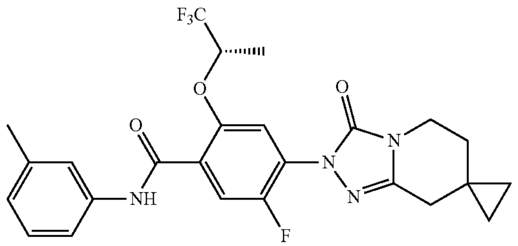 | 505.2 |
| 8 | 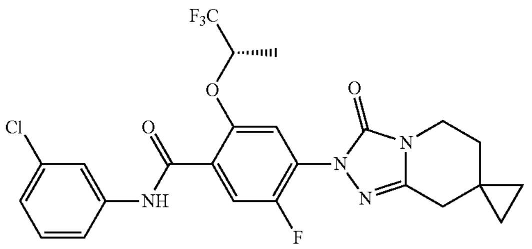 | 525.1 |
| 9 | 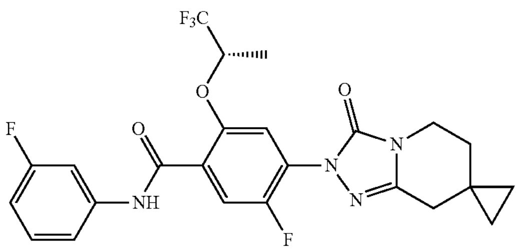 | 509.2 |

TABLE 1-continued
| Compound | Compound structure | [M + H]+ |
|---|---|---|
| 10 | 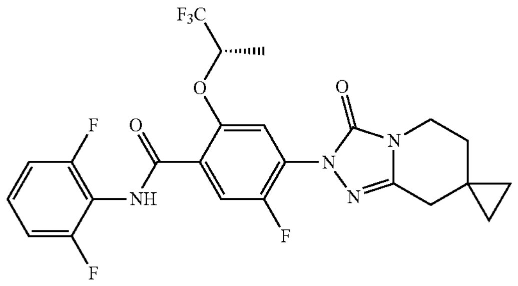 | 527.2 |
| 11 | 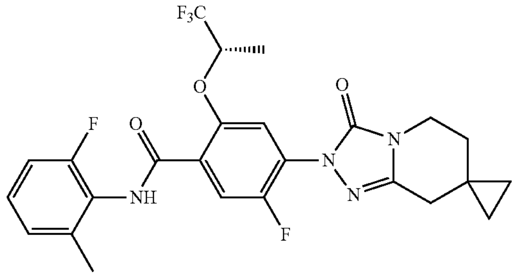 | 523.2 |
| 12 | 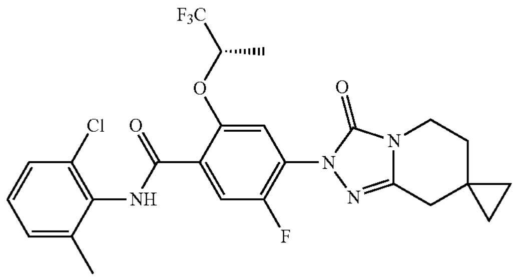 | 539.1 |
| 13 | 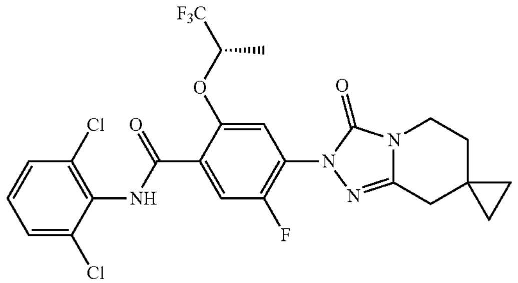 | 559.1 |
| 14 | 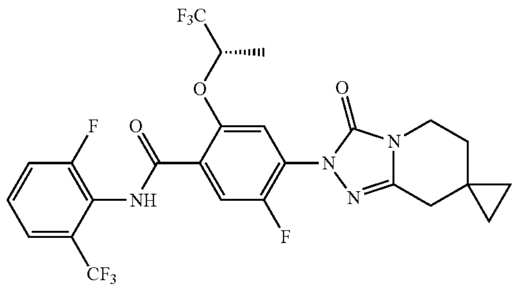 | 577.1 |

TABLE 1-continued
| Compound | Compound structure | [M + H]$^+$ |
|---|---|---|
| 15 | 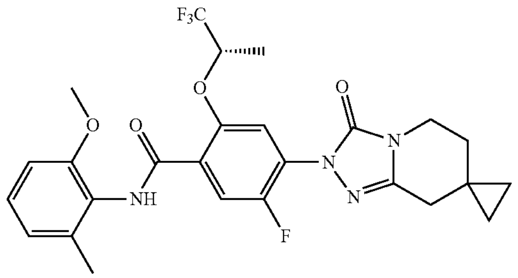 | 535.2 |
| 16 | 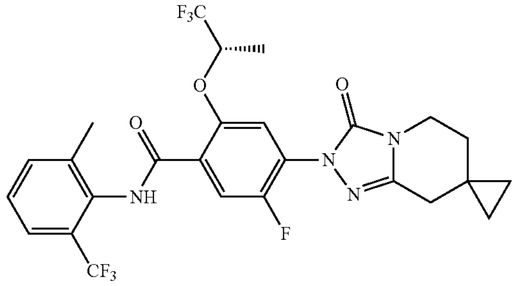 | 573.2 |
| 17 | 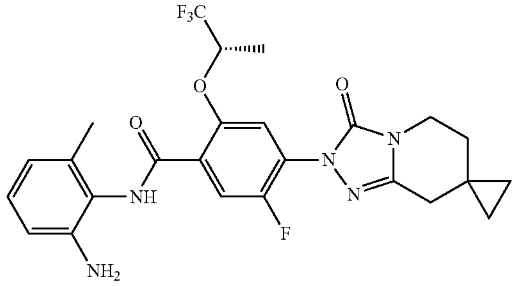 | 520.2 |
| 18 | 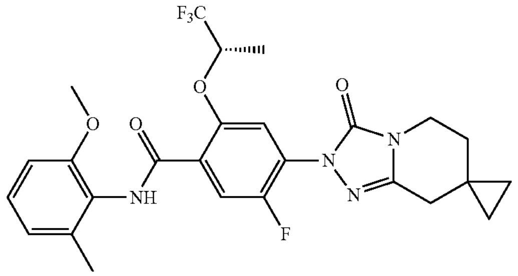 | 535.2 |
| 19 | 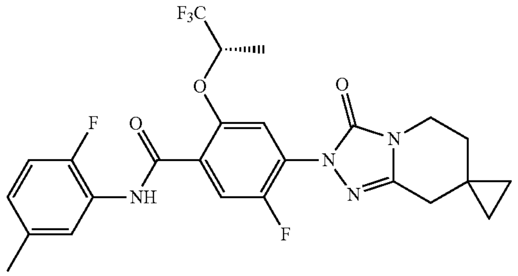 | 523.2 |

TABLE 1-continued
| Compound | Compound structure | [M + H]+ |
|---|---|---|
| 20 | 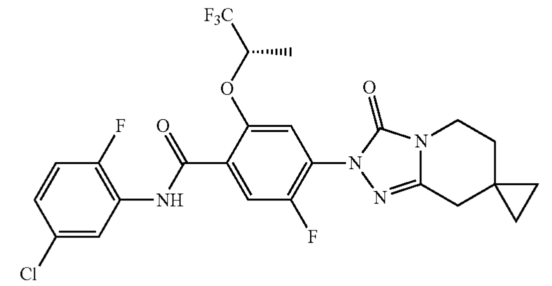 | 543.1 |
| 21 | 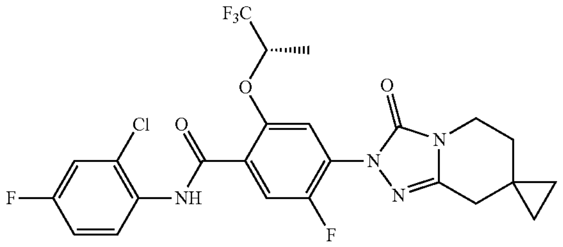 | 543.1 |
| 22 | 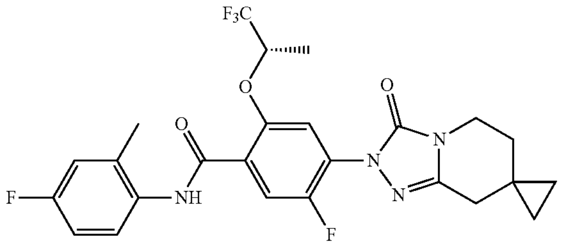 | 523.2 |
| 23 | 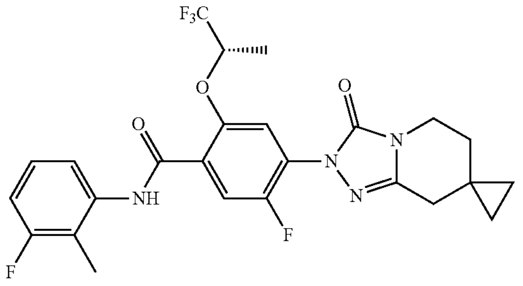 | 523.2 |
| 24 | 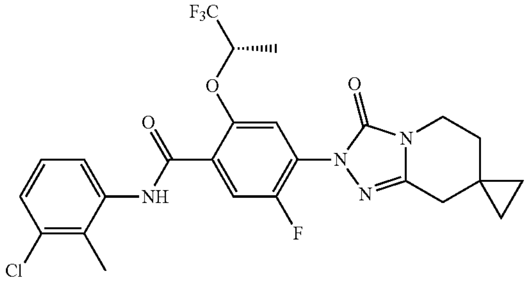 | 539.1 |

TABLE 1-continued
| Compound | Compound structure | $[M + H]^+$ |
|---|---|---|
| 25 | 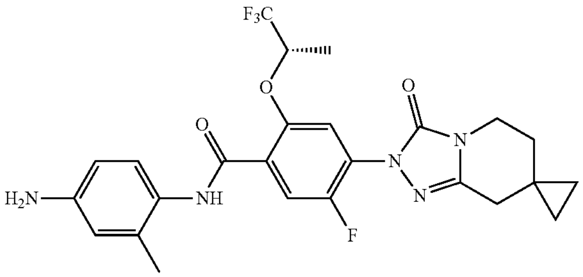 | 520.2 |
| 26 | 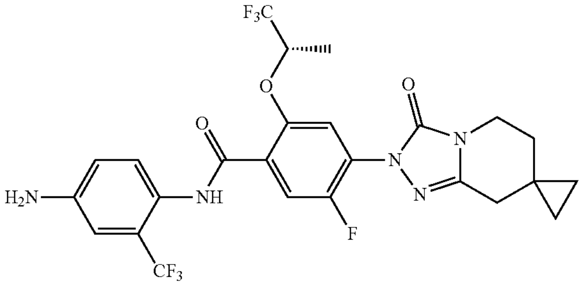 | 574.2 |
| 27 | 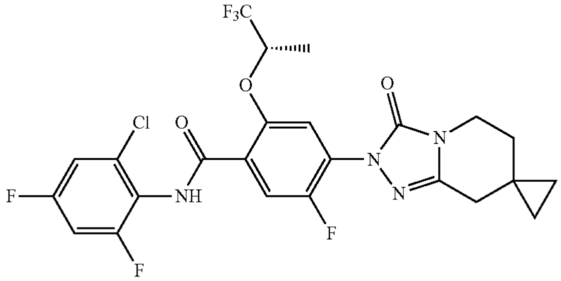 | 561.1 |
| 28 | 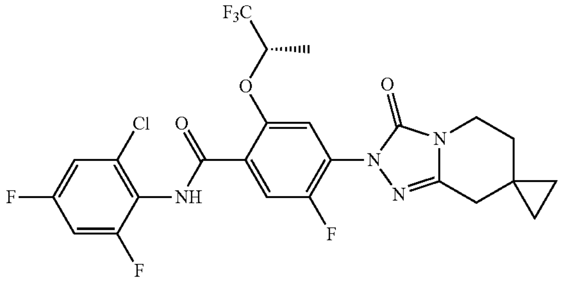 | 577.1 |
| 29 | 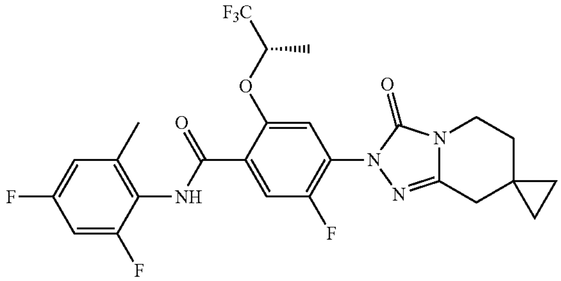 | 557.1 |

TABLE 1-continued
| Compound | Compound structure | [M + H]$^+$ |
|---|---|---|
| 30 | 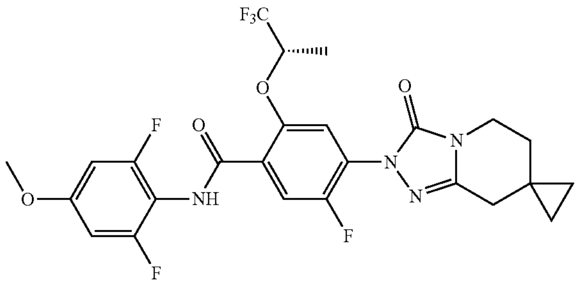 | 557.2 |
| 31 | 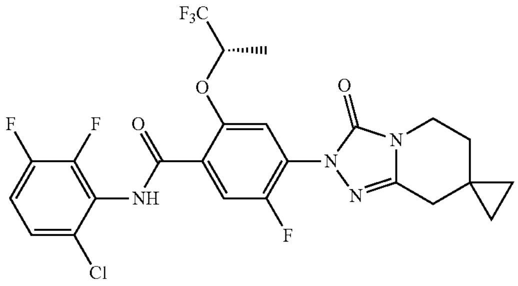 | 561.1 |
| 32 | 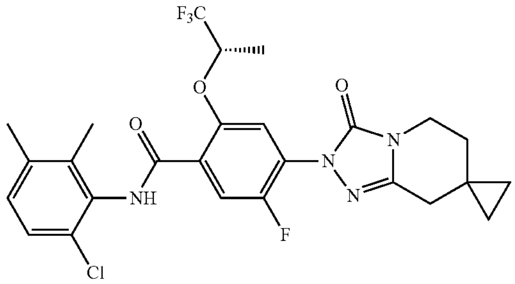 | 553.2 |
| 33 | 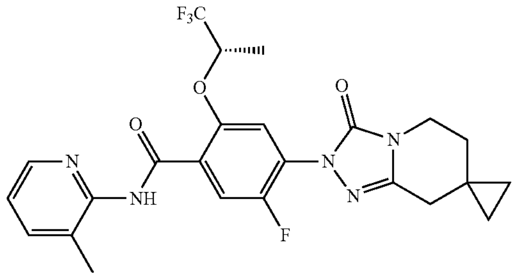 | 506.2 |
| 34 | 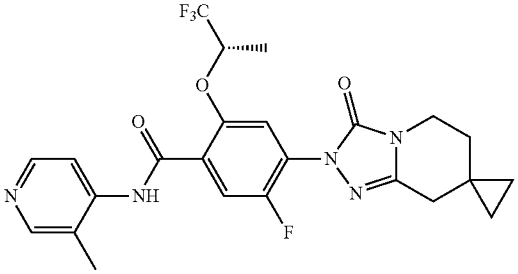 | 506.2 |

TABLE 1-continued
| Compound | Compound structure | [M + H]+ |
|---|---|---|
| 35 | 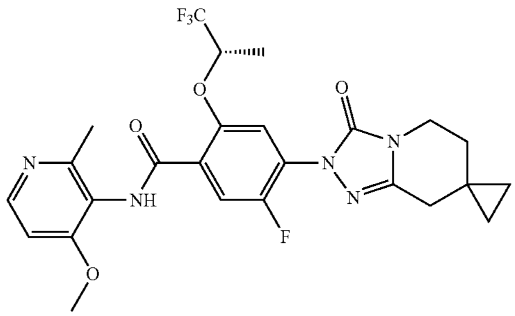 | 536.2 |
| 36 | 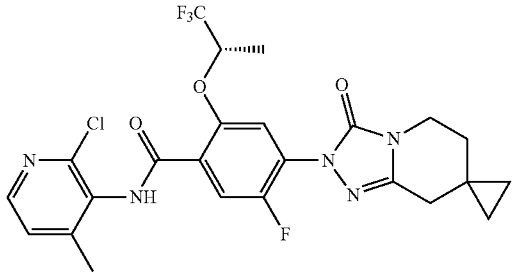 | 540.1 |
| 37 | 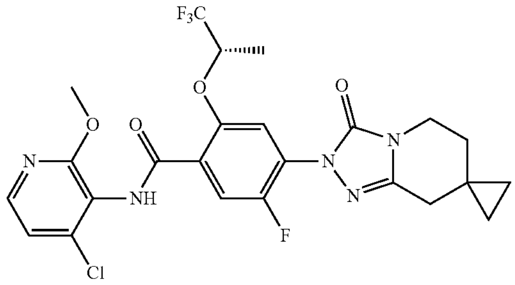 | 556.1 |
| 38 | 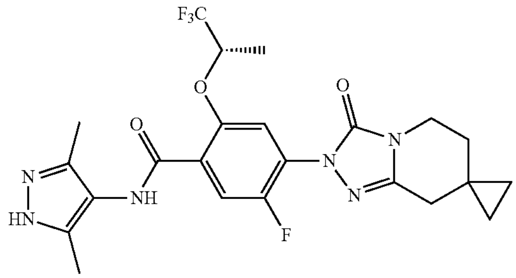 | 509.2 |
| 39 | 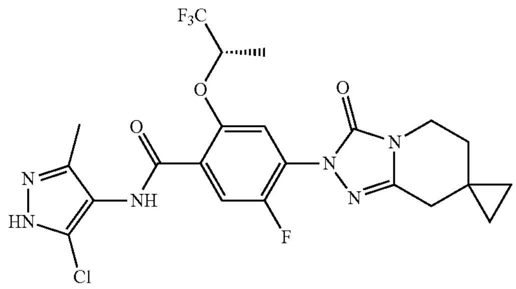 | 529.1 |

TABLE 1-continued
| Compound | Compound structure | [M + H]+ |
| --- | --- | --- |
| 40 | 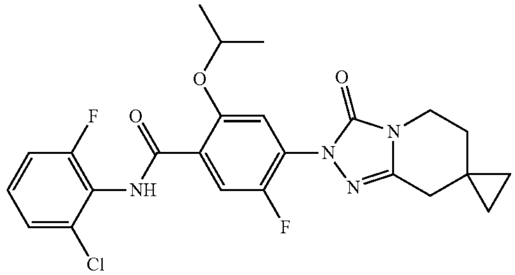 | 489.1 |
| 41 | 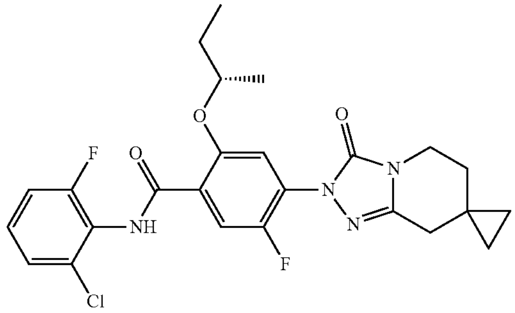 | 503.2 |
| 42 | 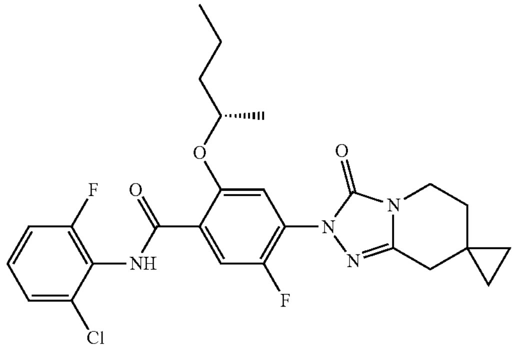 | 517.2 |
| 43 | 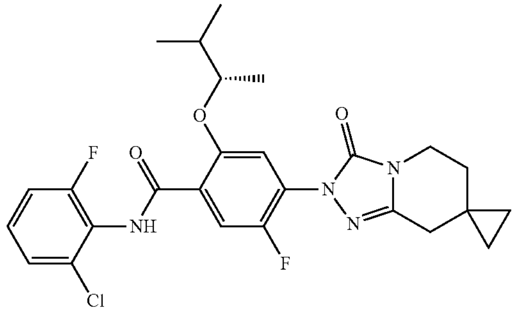 | 517.2 |
| 44 | 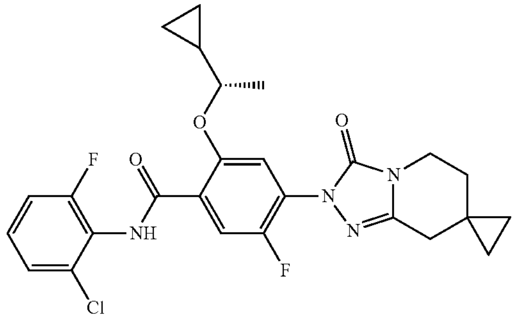 | 515.2 |

TABLE 1-continued
| Compound | Compound structure | [M + H]+ |
|---|---|---|
| 45 | 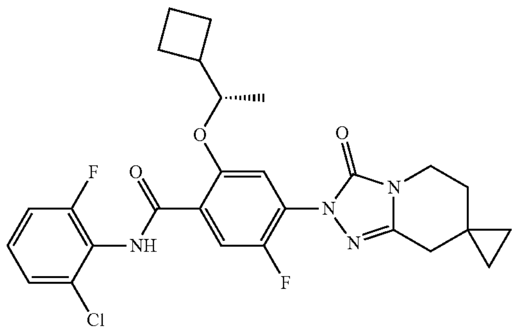 | 529.2 |
| 46 | 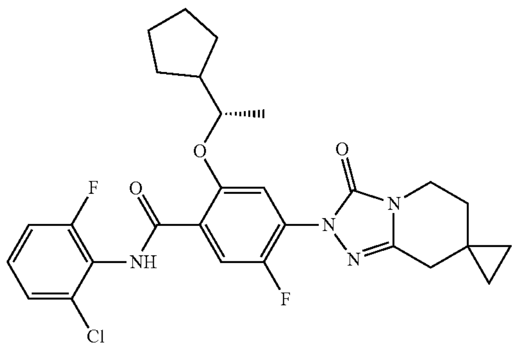 | 543.2 |
| 47 | 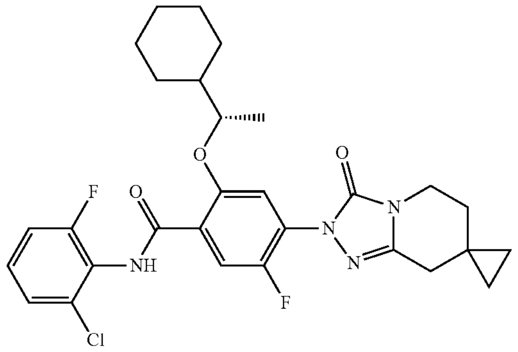 | 557.2 |
| 48 | 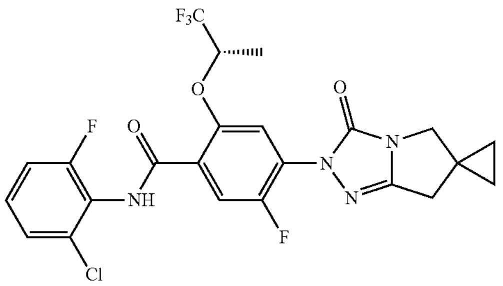 | 529.1 |

TABLE 1-continued
| Compound | Compound structure | [M + H]+ |
|---|---|---|
| 49 | 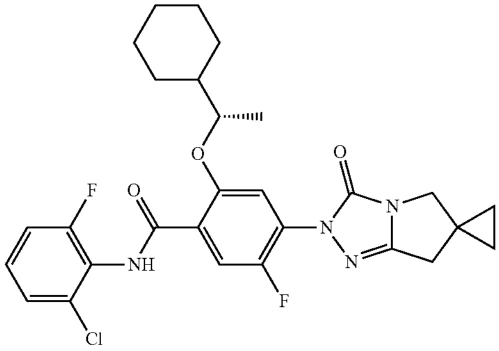 | 543.2 |
| 50 | 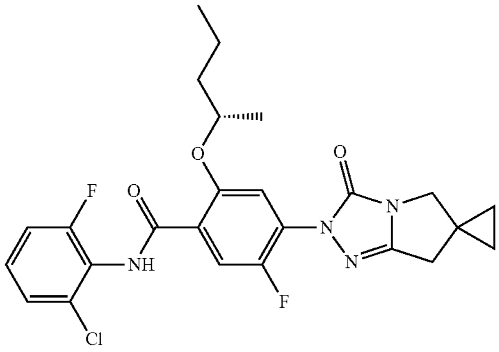 | 503.2 |
| 51 | 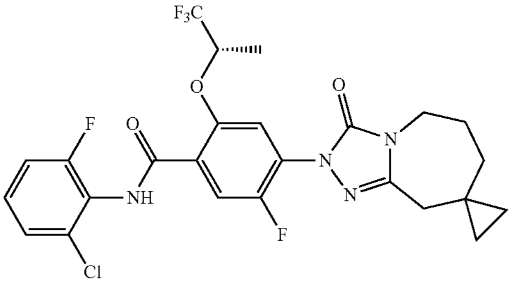 | 557.1 |
| 52 | 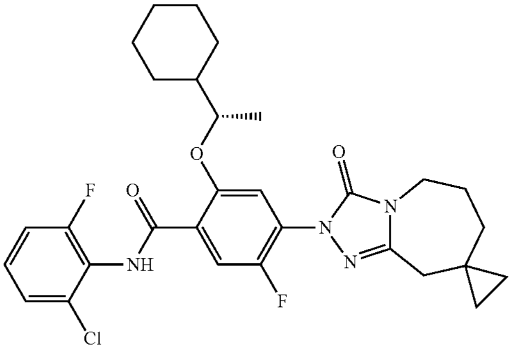 | 571.2 |

TABLE 1-continued

| Compound | Compound structure | [M + H]+ |
|---|---|---|
| 53 | 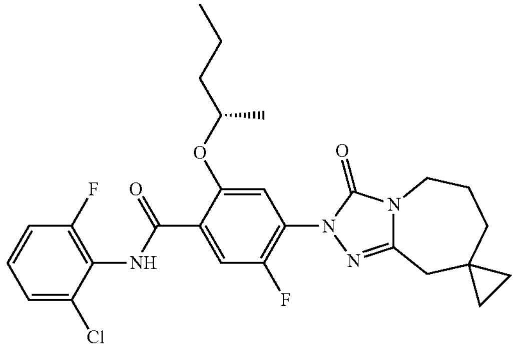 | 531.2 |

Example 54. Synthesis of (S)—N-(2-chloro-6-fluorophenyl)-5-fluoro-4-(3'-oxo-5',6'-dihydro-3'H-spiro[cyclopropane-1,7-[1,2,4]triazolo[4,3-α]pyridin]-2'(8'H)-yl)-2-((1,1,1-trifluoropropan-2-yl)oxy)benzamide (Compound 54)

54

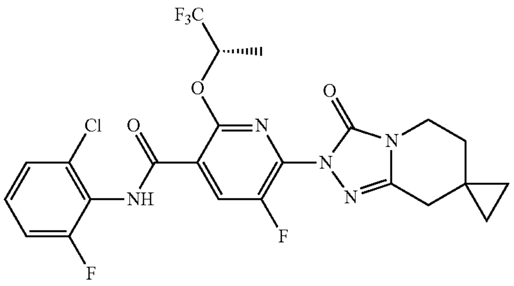

Synthetic Route:

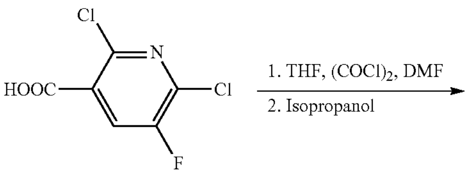

54-1

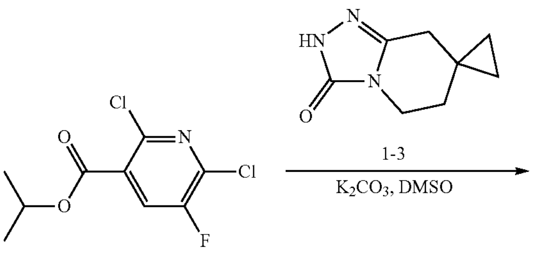

54-2

-continued

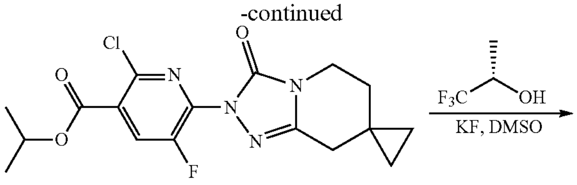

54-3

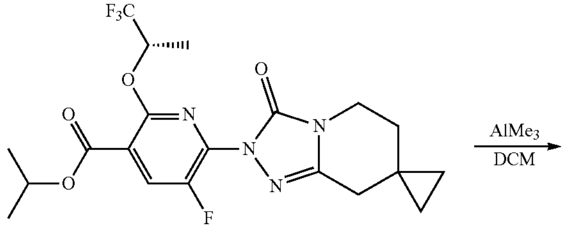

54-4

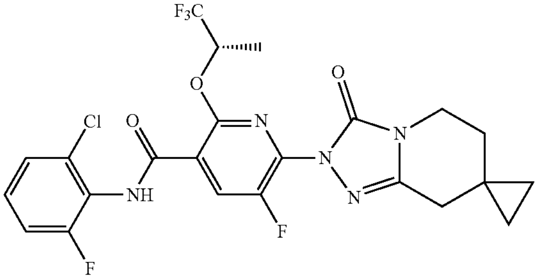

54

Step 1: Synthesis of Compound 54-2

54-1 (10 g, 47.62 mmol), THF (50 mL) and DMF (0.5 mL) were added to a 250 mL single-neck flask. The mixed solution was cooled to 0-5° C. in an ice bath under argon atmosphere, and then $(COCl)_2$ (6.35 g, 50 mmol) was added dropwise. After dropwise addition, the mixed solution was naturally heated to room temperature and stirred for reaction for 2 h. After the basic completion of the reaction as detected by LC-MS, the mixed solution was concentrated to dryness. The resulting residue was dissolved in THF (50 mL) for later use.

THF (40 mL), isopropanol (4.3 g, 71.43 mmol) and pyridine (4.5 g, 57.14 mmol) were added to another 250 mL single-neck flask. The mixed solution was cooled to 0-5° C. in an ice bath under argon atmosphere, and the THF solution obtained after the above reaction was added dropwise. After dropwise addition, the mixed solution was naturally heated to room temperature and stirred for reaction for 1 h. After the completion of the reaction as detected by LC-MS, EA (50 mL) and ice water (50 mL) were added to the mixed solution, the mixture was stirred, liquid separation was carried out, and the aqueous phase was extracted with EA (50 mL). The organic phases were combined, washed with saturated sodium chloride solution (50 mL), and concentrated at reduced pressure. The residue was purified by column chromatography (PE:EA=30:0 to 30:1) to give a product 54-2 as a colorless liquid (11.31 g, 94% yield), ESI-MS m/z: 252.0 $[M+H]^+$.

Step 2: Synthesis of Compound 54-3

54-2 (600 mg, 2.38 mmol), compound 1-3 (393 mg, 2.38 mmol), $K_2CO_3$ (493 mg, 3.57 mmol), and DMSO (10 mL) were added to a 100 mL single-neck flask, and the mixed solution was heated to 80° C. under argon atmosphere and stirred for reaction for 3 h. After the completion of the reaction as detected by LC-MS, EA (30 mL) and ice water (50 mL) were added to the mixed solution, the mixture was stirred, liquid separation was carried out, and the aqueous phase was extracted with EA (20 mL). The organic phases were combined, washed with saturated sodium chloride solution (20 mL), and concentrated at reduced pressure. The residue was purified by column chromatography (PE: EA=30:0 to 3:1 to 2:1) to give a product 54-3 as a yellow colloid (820 mg, 90% yield), ESI-MS m/z: 381.1 $[M+H]^+$.

Step 3: Synthesis of Compound 54-4

54-3 (820 mg, 2.153 mmol), (S)-1,1,1-trifluoropropan-2-ol (737 mg, 6.46 mmol), KF (375 mg, 6.46 mmol), and DMSO (10 mL) were added to a 100 mL single-neck flask, and the mixed solution was heated to 100° C. under argon atmosphere and stirred for reaction for 20 h. The reaction was not completed as detected by LC-MS. (S)-1,1,1-trifluoropropan-2-ol (368 mg, 3.23 mmol) was supplemented, and the mixed solution was stirred at a constant temperature for another 20 h. Then (S)-1,1,1-trifluoropropan-2-ol (368 mg, 3.23 mmol) was additionally supplemented, and the mixed solution was stirred at a constant temperature for 40 h. After the basic completion of the reaction as detected by LC-MS, EA (30 mL) and water (30 mL) were added to the mixed solution, the mixture was stirred, liquid separation was carried out, and the aqueous phase was extracted with EA (20 mL). The organic phases were combined, washed with saturated sodium chloride solution (20 mL), and concentrated at reduced pressure. The residue was purified by column chromatography (PE:EA=30:0 to 3:1 to 2:1) to give a product 54-4 as a light brown foamy solid (543 mg, 55% yield), ESI-MS m/z: 459.1 $[M+H]^+$.

Step 4: Synthesis of Compound 54

2-Chloro-6-fluoroaniline (685 mg, 4.712 mmol) and anhydrous DCM (10 mL) were added to a 250 mL three-necked flask. After the mixed solution was purged with argon, trimethylaluminum (4.7 ml, 1 M in n-heptane, 4.7 mmol) was added dropwise at room temperature. After dropwise addition, the mixed solution was stirred at room temperature for 2 h. Then 54-4 (540 mg, 1.178 mmol) was added. After being purged with argon, the mixed solution was heated to 50° C., and stirred for reaction for 3 h. After the completion of the reaction as detected by LC-MS, the reaction solution was slowly poured into saturated ammonium chloride solution (20 mL) in an ice bath. After the mixed solution was stirred for 30 min in an ice bath, liquid separation was carried out, and the aqueous phase was extracted with DCM (20 mL×3). The organic phases were combined, washed with saturated sodium chloride solution (20 mL), and concentrated, and the residue was purified by column chromatography (PE:EA=3:0 to 3:1 to 2:1) to give a product as an off-white foamy solid (455 mg, 71.1% yield), ESI-MS m/z: 544.0 $[M+H]^+$.

$^1H$ NMR (400 MHz, Chloroform-d) δ 9.10 (s, 1H), 8.54 (d, J=9.4 Hz, 1H), 7.27 (d, J=7.3 Hz, 2H), 7.14 (d, J=8.9 Hz, 1H), 5.97 (s, 1H), 3.78 (t, J=6.1 Hz, 2H), 2.68 (s, 2H), 1.82 (t, J=6.1 Hz, 2H), 1.67 (d, J=6.5 Hz, 3H), 0.62 (s, 4H).

Examples 55-59. Synthesis of Compounds 55-59

The target compounds 55-59 were obtained according to a similar synthesis method as in Example 54 using different starting materials.

TABLE 2

| Compound | Compound structure | $[M + H]^+$ |
|---|---|---|
| 55 | 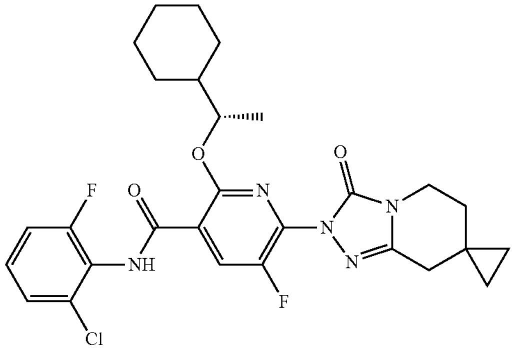 | 558.2 |

TABLE 2-continued
| Compound | Compound structure | [M + H]+ |
| --- | --- | --- |
| 56 | 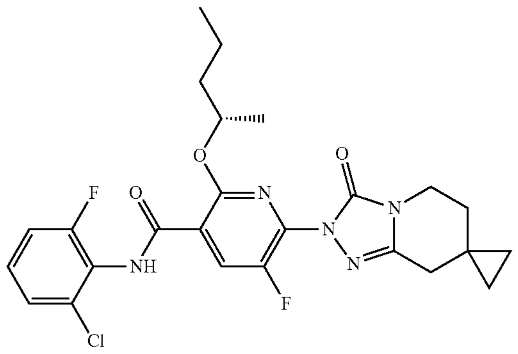 | 518.2 |
| 57 | 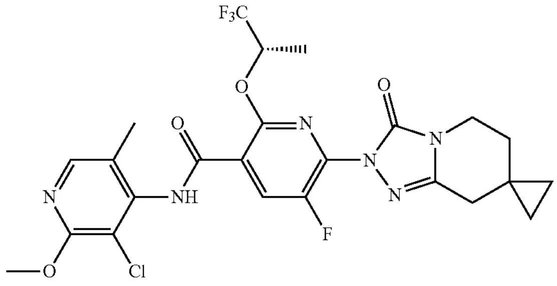 | 571.1 |
| 58 | 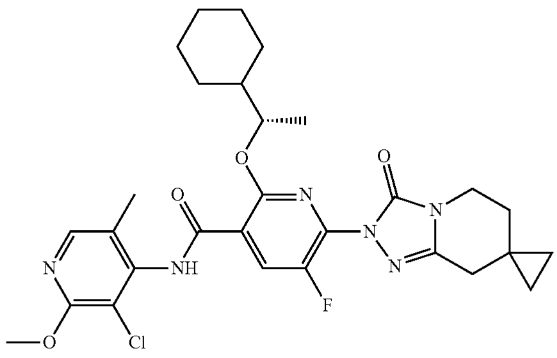 [SMILES: COc1ncc(C)c(NC(=O)c2cc(F)c(-n3nc4n(c3=O)CCC3(CC3)C4)nc2O[C@@H](C)C2CCCCC2)c1Cl] | 585.2 |
| 59 | 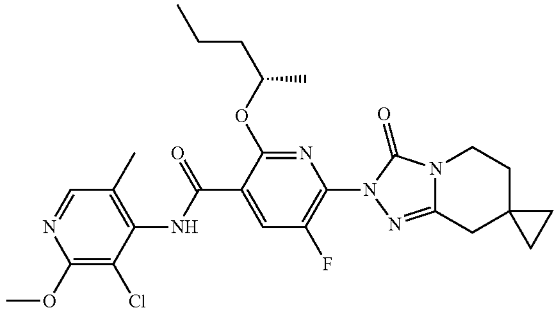 | 545.1 |

The reference compound used in the present invention is BAY-2402234, and the synthesis method therefor refers to patent WO2018077923. The reference compound has the following structure:

BAY-2402234

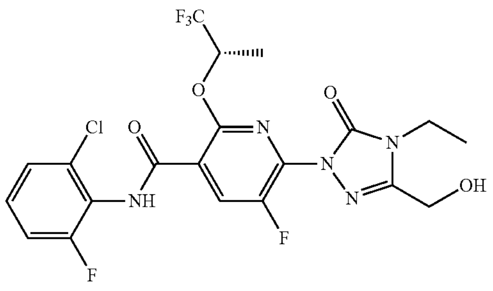

Example 60. Assay of Compounds of the Present Invention Against Enzyme Activity of DHODH The enzyme activity of DHODH was assayed through a cascade reaction to determine its ability to catalyze the oxidation of a natural substrate DHO (dihydroorotic acid) to orotic acid while reducing coenzyme Q. The enzyme activity of DHODH was indirectly detected by assaying the ability of the coenzyme Q to reduce a chromogenic substrate DCIP. After the compound and an enzyme reaction mixture were incubated for 5 min, a reaction substrate DHO was added to start the reaction, and the enzyme activity was assayed by assaying the absorption at 600 nm to detect the DCIP exhaustion in a timed manner. Compared with the control group, the DHODH enzyme activity inhibition rates of the compounds with different concentrations were calculated, and the median effective inhibitor concentration $IC_{50}$ values were calculated. The screening results are shown in Table 3.

Example 61. Assay of Anti-Proliferative Activity of Compounds of the Present Invention on THP-1 Cells THP-1 cells were seeded into a 384-well plate (Fisher 142762) at 3000 cells per well. The next day, serially diluted compounds were added, and 72 h after the addition, Cell-Titer-Lumi (Beyotime C0068XL) was added to measure the ATP content in the cells. The growth of the cells was evaluated, and $IC_{50}$ of the compounds against cell growth was calculated. The screening results are shown in Table 3.

Example 62. Assay of Anti-Proliferative Activity of Compounds of the Present Invention on MV-4-11 Cells MV-4-11 cells were seeded into a 384-well plate (Fisher 142762) at 3000 cells per well. The next day, serially diluted compounds were added, and 72 h after the addition, Cell-Titer-Lumi (Beyotime C0068XL) was added to measure the ATP content in the cells. The growth of the cells was evaluated, and $IC_{50}$ of the compounds against cell growth was calculated. The screening results are shown in Table 3.

TABLE 3

Inhibitory activity of the compounds of the present invention against DHODH enzyme, and anti-proliferative activity of THP-1 cells and MV-4-11 cells

| Compound | DHODH enzyme activity $IC_{50}$ (nM) | Cell anti-proliferative activity $IC_{50}$ (nM) THP-1 | MV-4-11 |
|---|---|---|---|
| 1 | A | 27.56 | 1.27 |
| 2 | A | — | 4.56 |
| 3 | A | — | 5.45 |
| 4 | A | — | A |
| 5 | A | — | A |
| 6 | A | — | A |
| 7 | A | — | A |
| 8 | A | — | A |
| 9 | A | — | A |
| 10 | A | — | 2.24 |
| 11 | A | — | 2.13 |
| 12 | A | — | 1.45 |
| 13 | A | — | 1.56 |
| 14 | A | — | A |
| 15 | A | — | 3.42 |
| 16 | A | — | A |
| 17 | A | — | A |
| 18 | A | — | A |
| 19 | A | — | A |
| 20 | A | — | A |
| 21 | A | — | A |
| 22 | A | — | A |
| 23 | A | — | A |
| 24 | A | — | A |
| 25 | A | — | A |
| 26 | A | — | A |
| 27 | A | — | A |
| 28 | A | — | A |
| 29 | A | — | A |
| 30 | A | — | A |
| 31 | A | — | A |
| 32 | A | — | A |
| 33 | A | — | B |
| 34 | A | — | 10.23 |
| 35 | A | — | 6.79 |
| 36 | A | — | 12.45 |
| 37 | A | — | 10.54 |
| 38 | A | — | 21.36 |
| 39 | A | — | 65.78 |
| 40 | A | — | A |
| 41 | A | — | A |
| 42 | A | — | A |
| 43 | A | — | A |
| 44 | A | — | A |
| 45 | A | — | A |
| 46 | A | — | A |
| 47 | A | — | A |
| 48 | A | — | 10.69 |
| 49 | A | — | A |
| 50 | A | — | A |
| 51 | A | 47.56 | 5.45 |
| 52 | A | — | A |
| 53 | A | — | 6.89 |
| 54 | A | 24.53 | 0.51 |
| 55 | A | — | 1.45 |
| 56 | A | — | 1.97 |
| 57 | A | — | 0.32 |
| 58 | A | — | 0.75 |
| 59 | A | — | 2.05 |
| BAY-2402234 | A | 35.6 | 3.82 |

A represents $IC_{50}$ ≤50 nM
B represents 50 nM ≤ $IC_{50}$ ≤ 0.5 μM
C represents $IC_{50}$ >0.5 μM As can be seen from the data in the table above, the compounds of the present invention inhibit the DHODH enzyme and also have strong anti-proliferative activity on THP-1 and MV-4-11 tumor cells. Compared with the control compound, the compounds of the present invention have greatly improved inhibitory activity against MV-4-11 cells.

Example 63. Pharmacokinetic Evaluation in Mice

The compounds were administered by intravenous injection at a dose of 2 mg/kg and oral gavage at a dose of 10 mg/kg (0.5% CMC-Na suspension). 15 male ICR mice were selected, and each mouse was subjected to blood collection at 3 discrete time points, with 3 mice per time point. The time points of sampling were as follows: before administration, and 5 min, 15 min, 30 min, 1 h, 3 h, 5 h, 8 h, 12 h and 24 h after administration. 80 μL of blood was collected from the orbits or hearts of the mice at each time point after administration. All whole blood samples were collected in tubes containing $EDTAK_2$ and centrifuged (1500-1600 rmp/min) at 4° C. for 10 min to isolate plasma, which was then stored in a refrigerator at −90° C. to −60° C. for sample analysis. The compound concentration in the plasma was determined by liquid chromatography-tandem mass spectrometry, and the corresponding pharmacokinetic parameters were obtained according to a plasma concentration-time curve.

TABLE 4

Pharmacokinetic parameters of compound 1 in mice

| Compound | Route of Administration | Dose (mg/kg) | $t_{1/2}$ (h) | $T_{max}$ (h) | $C_{max}$ (ng/mL) | $AUC_{0-t}$ (ng · h/L) | Vss (L/kg) | Cl (mL/h/kg) | F (%) |
|---|---|---|---|---|---|---|---|---|---|
| 1 | iv | 2 | 1.79 | NA | NA | 2530 | 1.66 | 13.2 | NA |
| | po | 10 | 2.07 | 0.25 | 2240 | 7780 | NA | NA | 61.7 |

NA indicates that the data are not available

As can be seen from the data in the table above, compound 1 has good oral bioavailability, and good oral absorption properties are of great significance in improving the efficacy of drugs, reducing the dose of administration and reducing the costs.

Although specific embodiments of the present invention have been described above, it will be appreciated by those skilled in the art that these embodiments are merely illustrative and that many changes or modifications can be made to these embodiments without departing from the principles and spirit of the present invention. The protection scope of the present invention is therefore defined by the appended claims.

The invention claimed is:

1. A compound of general formula (1) or an isomer, a crystalline form, a pharmaceutically acceptable salt, a hydrate or a solvate thereof:

(1)

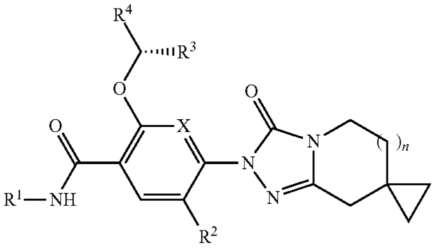

wherein in general formula (1):

n is 0, 1 or 2;

X is CH or N;

$R^1$ is aryl or heteroaryl, wherein the aryl and heteroaryl may be substituted with one or more of the following groups: halogen, $NH_2$, C1-C3 alkyl, C1-C3 alkoxy or halogenated C1-C3 alkyl;

$R^2$ is H or F;

$R^3$ is C1-C3 alkyl;

$R^4$ is C1-C6 alkyl, C3-C8 cycloalkyl or halogenated C1-C6 alkyl.

2. The compound or the isomer, the crystalline form, the pharmaceutically acceptable salt, the hydrate or the solvate thereof according to claim 1, wherein in general formula (1), $R^1$ is

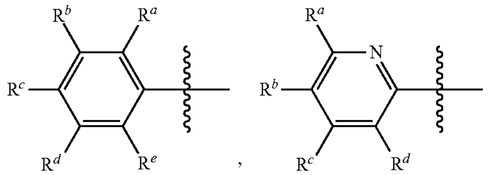

-continued

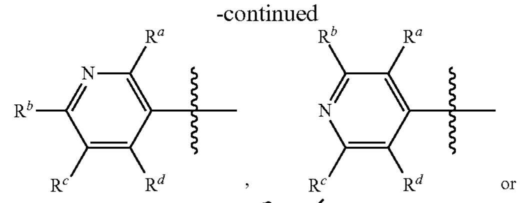

or

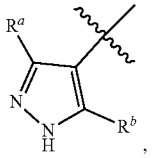

wherein $R^a$, $R^b$, $R^c$, $R^d$ and $R^e$ are independently H, F, Cl, Me, Et, OMe, $CHF_2$, $CF_3$ or $NH_2$.

3. The compound or the isomer, the crystalline form, the pharmaceutically acceptable salt, the hydrate or the solvate thereof according to claim 1, wherein in general formula (1), $R^3$ is Me.

4. The compound or the isomer, the crystalline form, the pharmaceutically acceptable salt, the hydrate or the solvate thereof according to claim 1, wherein in general formula (1), $R^4$ is Me, Et, $CF_3$,

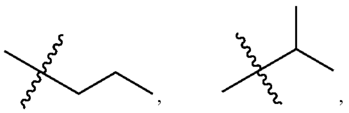

-continued
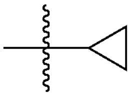,
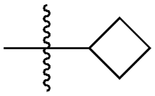,
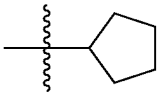
or
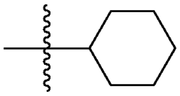.
5. The compound or the isomer, the crystalline form, the pharmaceutically acceptable salt, the hydrate or the solvate thereof according to claim 1, wherein the compound has one of the following structures:
1
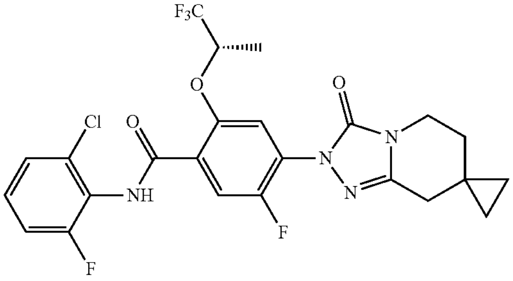
2
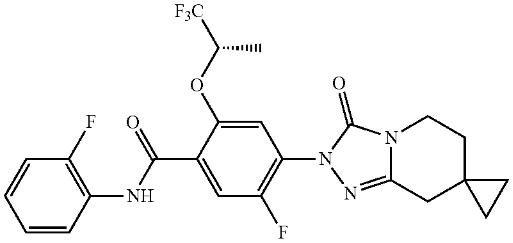
3
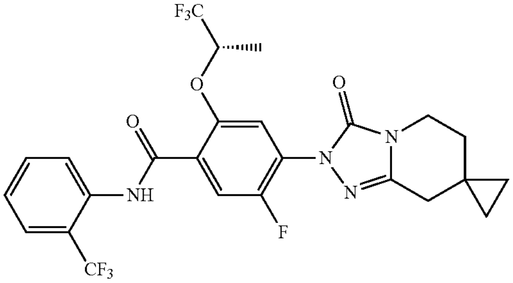
4
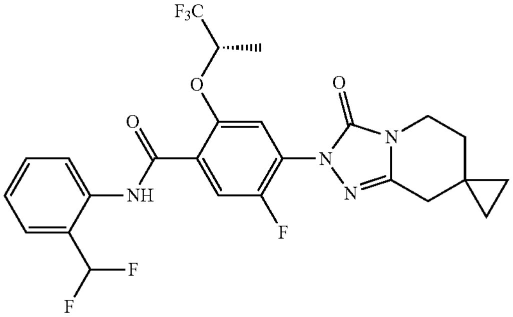
-continued
5
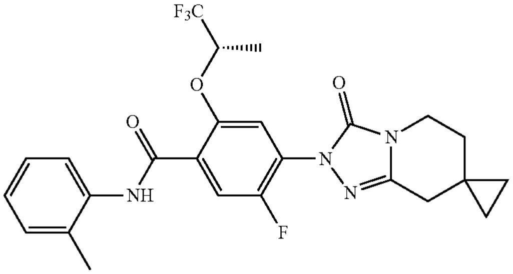
6
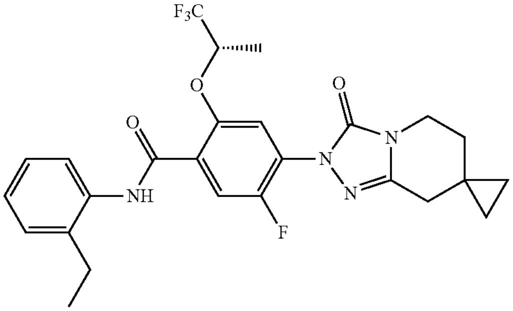
7
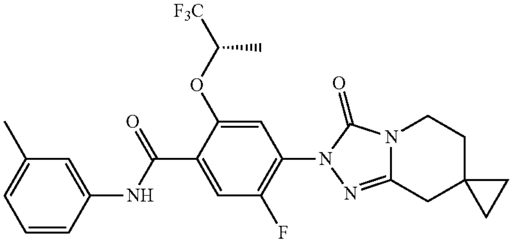
8
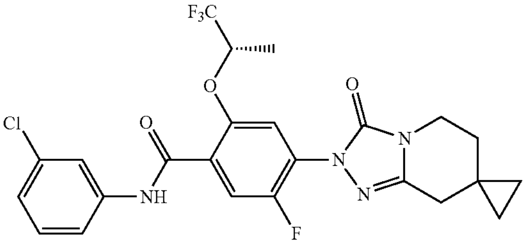
9
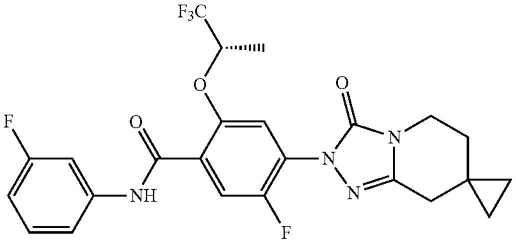
10
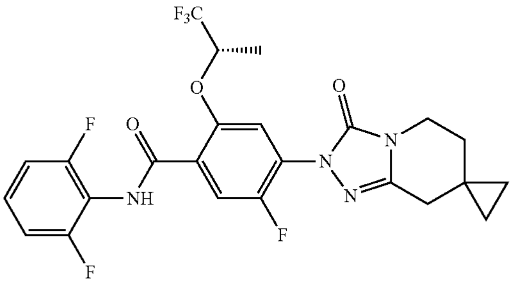

-continued
11
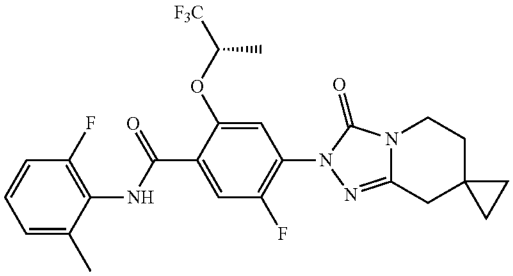
12
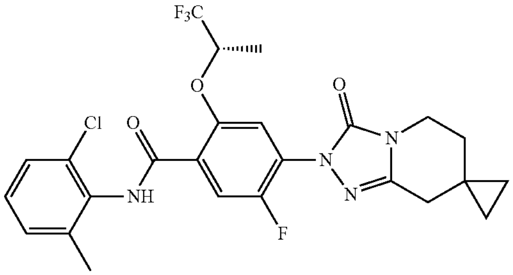
13
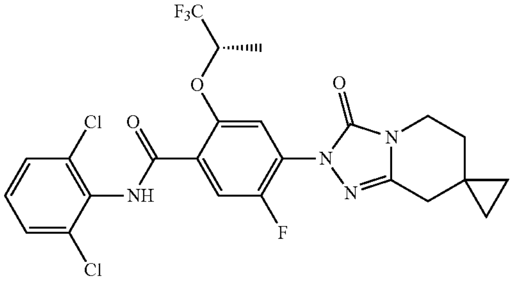
14
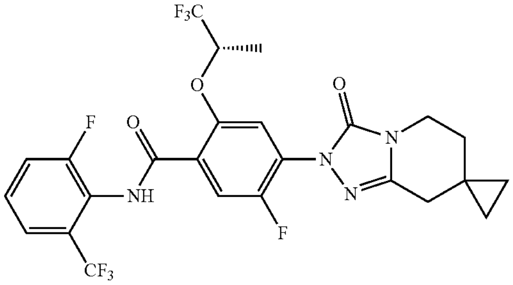
15
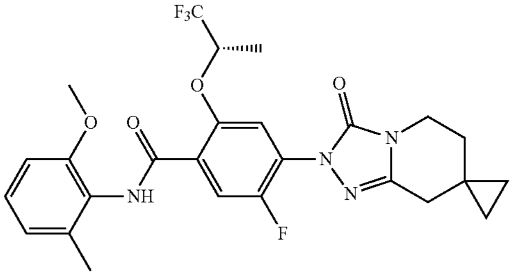
-continued
16
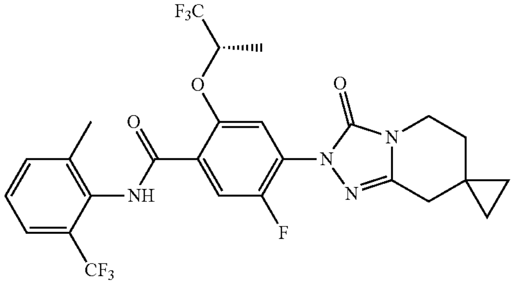
17
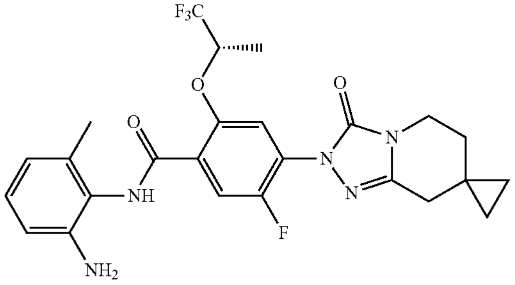
18
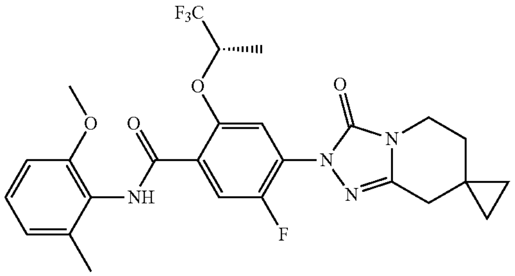
19
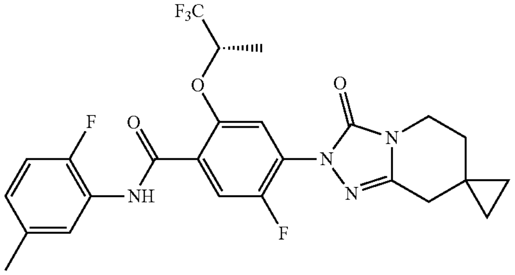
20
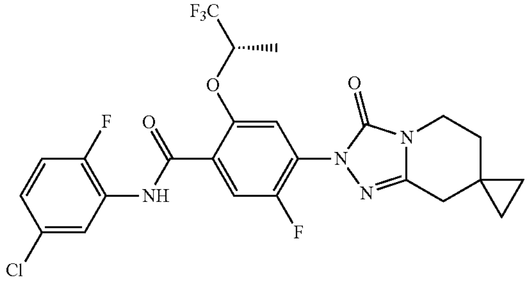

-continued
21
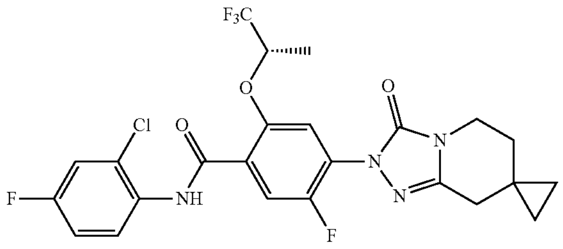
22
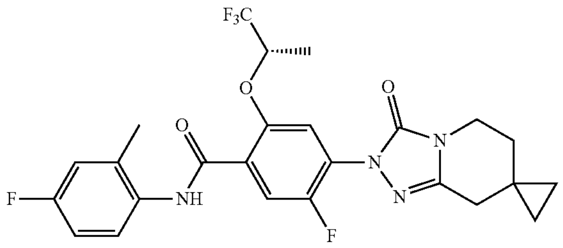
23
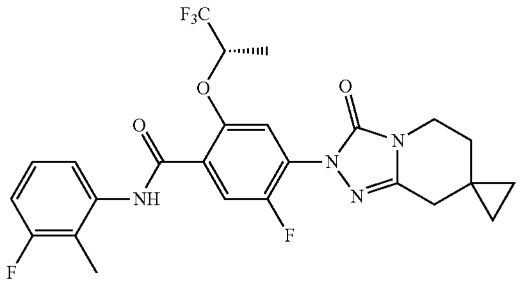
24
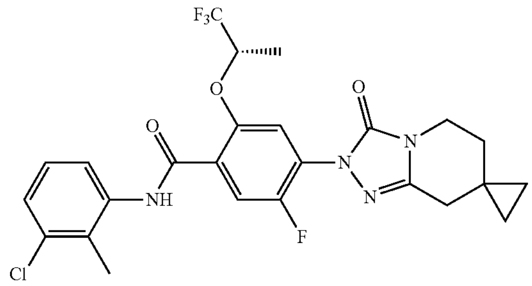
25
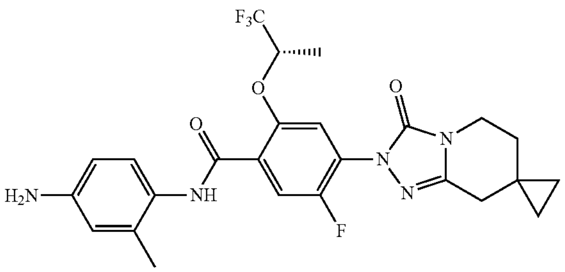
-continued
26
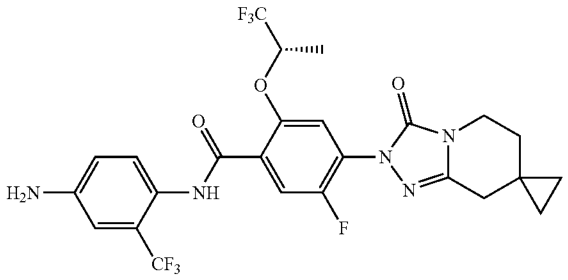
27
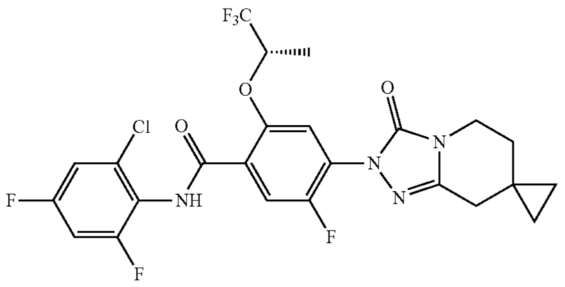
28
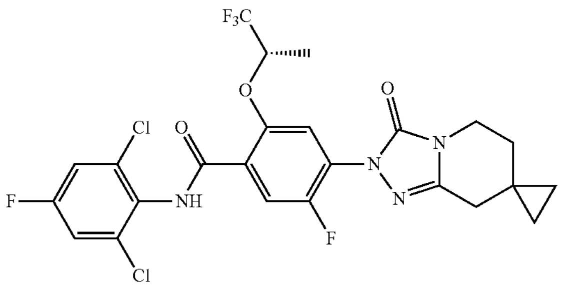
29
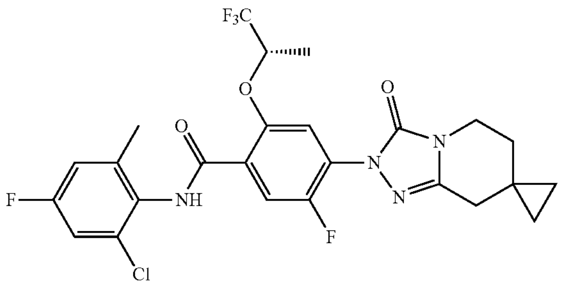
30
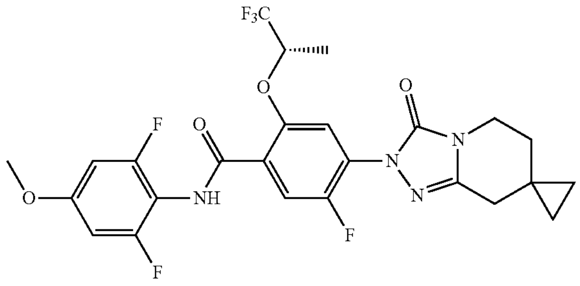

-continued
31
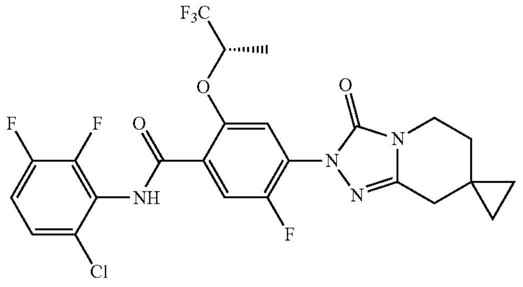
32
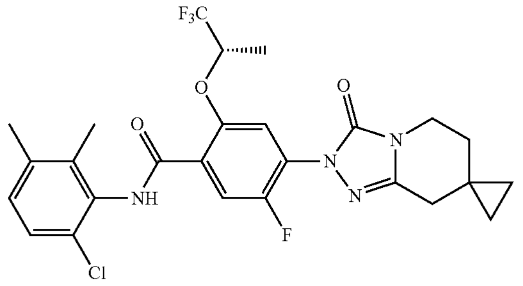
33
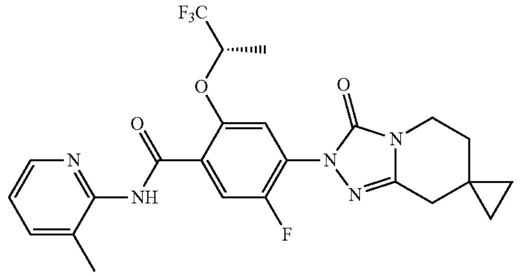
34
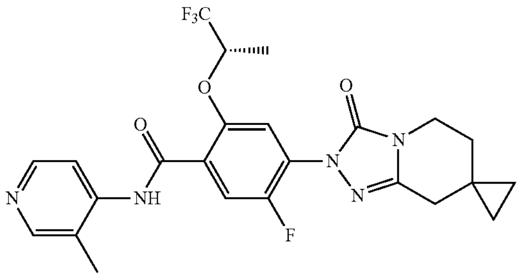
35
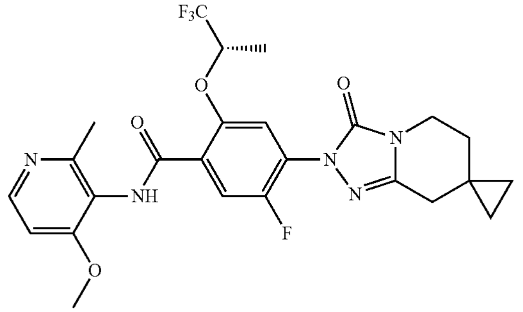
-continued
36
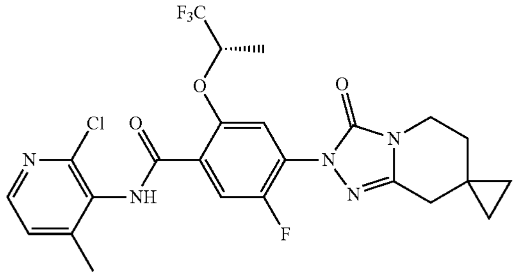
37
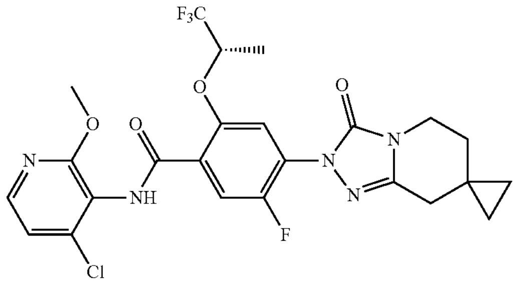
38
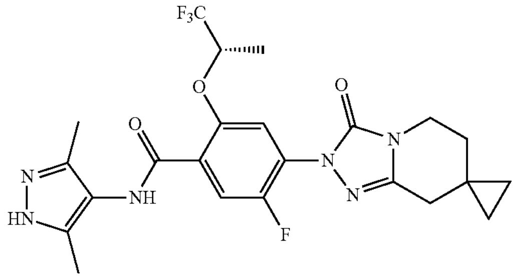
39
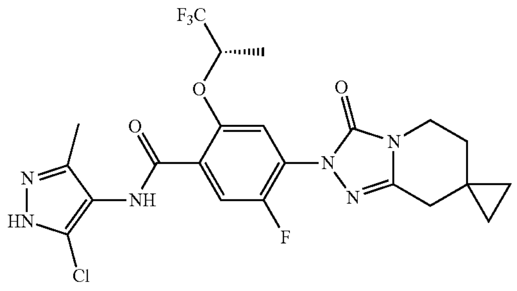
40
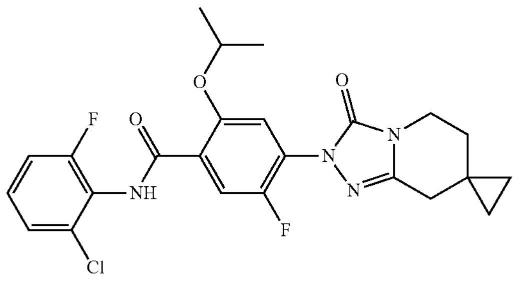

-continued
41
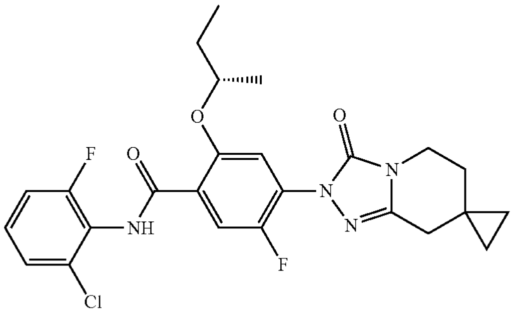
42
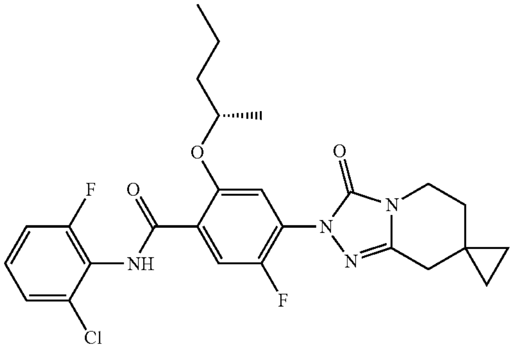
43
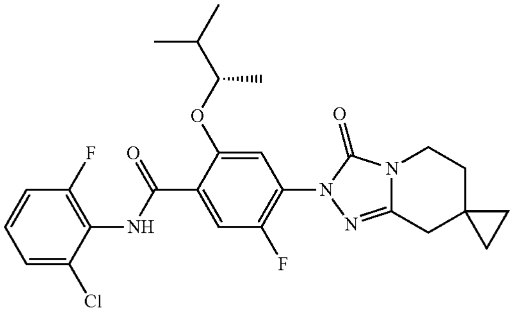
44
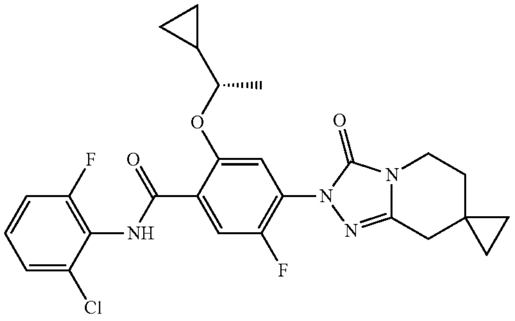
45
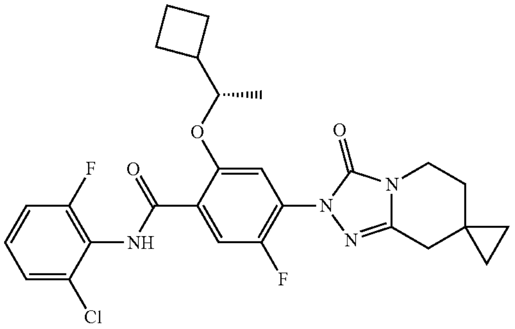
-continued
46
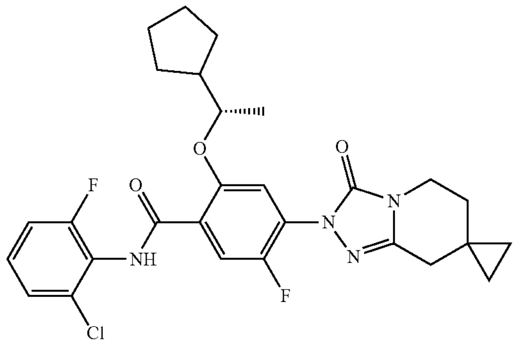
47
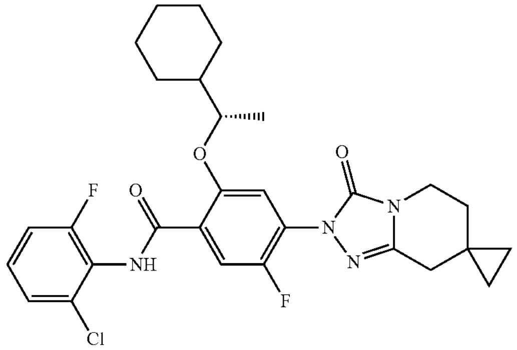
48
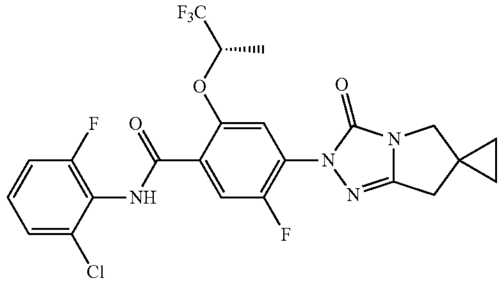
49
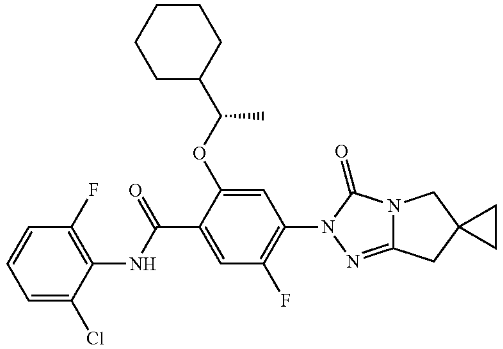

-continued
50
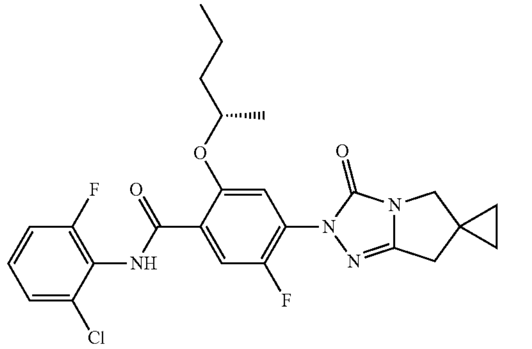
51
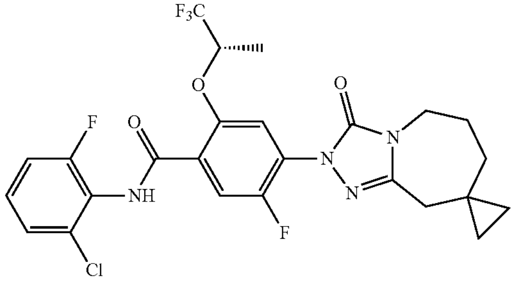
52
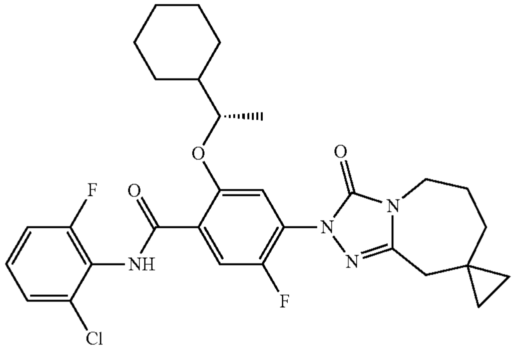
53
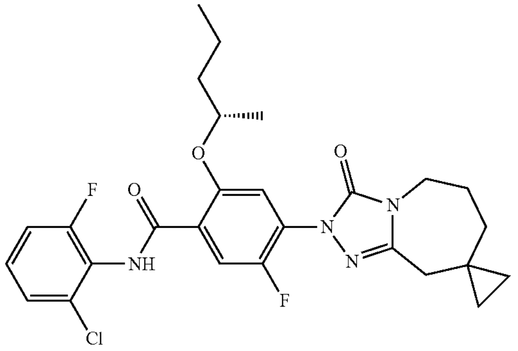
54
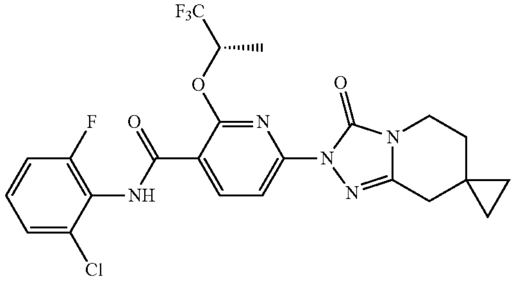
-continued
55
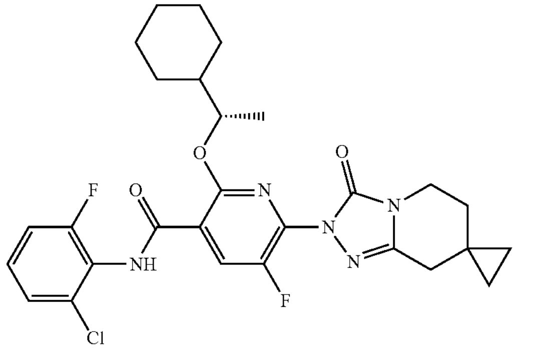
56
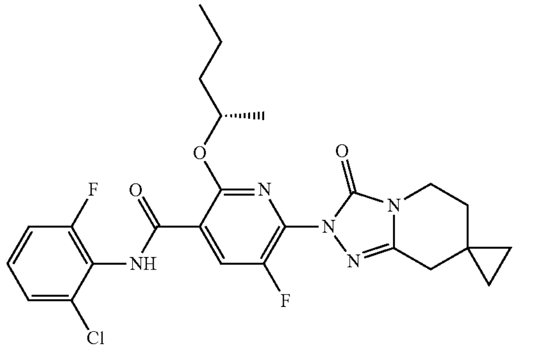
57
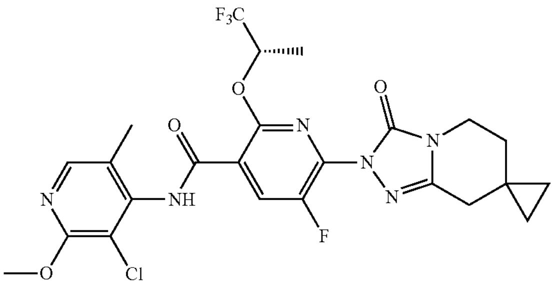
58
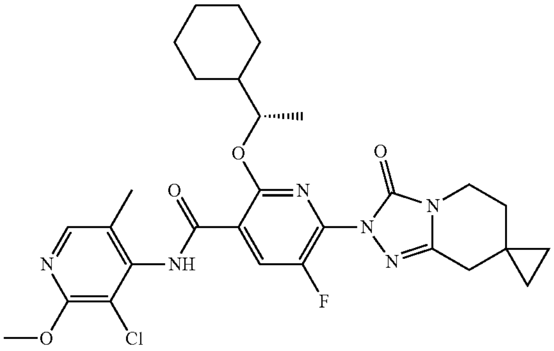

-continued
59
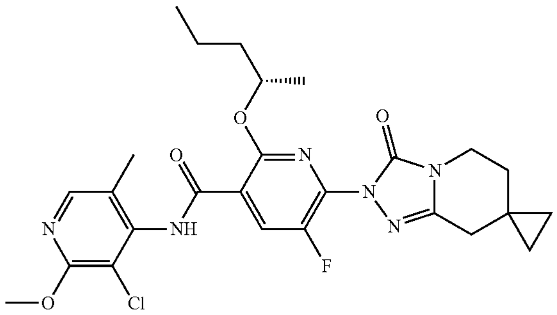 [SMILES: CCC[C@H](C)Oc1nc(-n2nc3n(c2=O)CCC2(CC2)C3)c(F)cc1C(=O)Nc1c(C)cnc(OC)c1Cl]
6. A pharmaceutical composition, comprising a pharmaceutically acceptable excipient or carrier; and the compound or the isomer, the crystalline form, the pharmaceutically acceptable salt, the hydrate or the solvate thereof according to claim 1 as an active ingredient.
* * * * *